(12) United States Patent
de Rodas et al.

(10) Patent No.: US 10,172,376 B2
(45) Date of Patent: *Jan. 8, 2019

(54) METHODS FOR FEEDING SOWS AND FOR IMPROVING THE HEALTH OF YOUNG PIGLETS

(71) Applicant: PURINA ANIMAL NUTRITION LLC, Shoreview, MN (US)

(72) Inventors: Brenda de Rodas, O'Fallon, MO (US); Cindie M. Luhman, Webster Groves, MO (US); Bill L. Miller, Labadie, MO (US); Paul A. Porter, Webster Grovers, MO (US)

(73) Assignee: PURINA ANIMAL NUTRITION LLC, Shoreview, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/254,159

(22) Filed: Sep. 1, 2016

(65) Prior Publication Data

US 2016/0366908 A1 Dec. 22, 2016

Related U.S. Application Data

(63) Continuation of application No. 14/788,922, filed on Jul. 1, 2015, now Pat. No. 9,433,232, which is a continuation of application No. 13/973,486, filed on Aug. 22, 2013, now Pat. No. 9,078,457, which is a continuation of application No. 10/349,743, filed on Jan. 22, 2003, now Pat. No. 8,519,008.

(51) Int. Cl.
| | |
|---|---|
| A23K 1/18 | (2006.01) |
| A23K 20/10 | (2016.01) |
| A01K 9/00 | (2006.01) |
| A61K 31/047 | (2006.01) |
| A23K 50/30 | (2016.01) |
| A23K 10/30 | (2016.01) |
| A61K 9/00 | (2006.01) |
| A61K 47/46 | (2006.01) |

(52) U.S. Cl.
CPC ............... *A23K 20/10* (2016.05); *A01K 9/00* (2013.01); *A23K 10/30* (2016.05); *A23K 50/30* (2016.05); *A61K 9/0056* (2013.01); *A61K 31/047* (2013.01); *A61K 47/46* (2013.01)

(58) Field of Classification Search
None
See application file for complete search history.

(56) References Cited

U.S. PATENT DOCUMENTS

| | | | |
|---|---|---|---|
| 2,876,157 A | 3/1959 | Selden | |
| 3,105,791 A | 10/1963 | Banford et al. | |
| 3,338,718 A | 8/1967 | Olson et al. | |
| 3,463,860 A * | 8/1969 | Schulman | A61K 31/215 514/544 |
| 3,686,392 A | 8/1972 | Hamada et al. | |
| 3,715,433 A | 2/1973 | Bauernfeind et al. | |
| 3,723,130 A | 3/1973 | Stephenson et al. | |
| 3,726,254 A | 4/1973 | Conover | |
| 3,794,732 A | 2/1974 | Raun | |
| 3,852,473 A | 12/1974 | Baile et al. | |
| 3,857,971 A | 12/1974 | Abdo et al. | |
| 3,875,304 A | 4/1975 | Hunt et al. | |
| 3,928,571 A | 12/1975 | Raun | |
| 3,935,316 A | 1/1976 | Moon | |
| 3,956,482 A | 5/1976 | Hahn et al. | |
| 3,959,493 A | 5/1976 | Baalsrud et al. | |
| 3,962,462 A | 6/1976 | Burkwall, Jr. et al. | |
| 3,975,513 A | 8/1976 | Hecht et al. | |
| 3,984,576 A | 10/1976 | Burkwall, Jr. et al. | |
| 4,005,211 A | 1/1977 | Marsboom | |
| 4,011,345 A | 3/1977 | Bartsch | |
| 4,055,681 A | 10/1977 | Balaz et al. | |
| 4,059,691 A | 11/1977 | Willard, Sr. | |
| 4,087,556 A | 5/1978 | Harte | |
| 4,095,000 A | 6/1978 | Brenner | |
| 4,120,952 A | 10/1978 | Cardon | |
| 4,125,629 A | 11/1978 | Rossi | |
| 4,127,676 A | 11/1978 | Merensalmi | |
| 4,127,678 A | 11/1978 | Burkwall, Jr. | |
| 4,136,167 A | 1/1979 | Parry et al. | |
| 4,161,543 A | 7/1979 | Glabe et al. | |
| 4,181,709 A | 1/1980 | Dannelly | |

(Continued)

FOREIGN PATENT DOCUMENTS

| | | |
|---|---|---|
| CA | 600707 | 6/1960 |
| CA | 645019 | 7/1962 |

(Continued)

OTHER PUBLICATIONS

Feeding the Lactating Sow (Nov. 20, 2001).*
Peak Plus 37 Product Information Sheet (Land O' Lakes Product Manual, revised Jan. 1, 2003).*
QLF Liquid feed supplements information sheet (www.qlf.com, accessed on May 17, 2017).*
Peak Plus 37 Product Information Sheet (Land O' Lakes Product Manual, revised Jan. 1, 2003). (Year: 2003).*
QLF Liquid feed supplements information sheet (www.qlf.com, accessed on May 17, 2017) (Year: 2017).*

(Continued)

*Primary Examiner* — Robert A Wax
*Assistant Examiner* — Melissa Mercier
(74) *Attorney, Agent, or Firm* — Dorsey & Whitney LLP

(57) ABSTRACT

A method of improving the health of a first group of young monogastric mammals, the first group of young monogastric mammals nursing from a first lactating monogastric mammal during a pre-weaning period, the method including feeding the first lactating monogastric mammal an effective amount of an animal feed during the pre-weaning period, and feeding the first lactating monogastric mammal an effective amount of sugar alcohol during the pre-weaning period.

16 Claims, No Drawings

(56) References Cited

U.S. PATENT DOCUMENTS

| | | |
|---|---|---|
| 4,186,212 A | 1/1980 | Howell |
| 4,212,896 A | 7/1980 | Brown, Jr. et al. |
| 4,228,195 A | 10/1980 | Priegnitz |
| 4,247,562 A | 1/1981 | Bernotavicz |
| 4,289,784 A | 9/1981 | Bochis et al. |
| 4,320,116 A | 3/1982 | Bjorck |
| 4,336,250 A | 6/1982 | Scheifinger |
| 4,349,544 A | 9/1982 | Cort et al. |
| 4,353,902 A | 10/1982 | Hedde et al. |
| 4,380,551 A | 4/1983 | Frontczak |
| 4,410,551 A | 10/1983 | Comer |
| 4,423,072 A | 12/1983 | Stahly |
| 4,469,672 A | 9/1984 | Harris |
| 4,495,208 A | 1/1985 | Friedman et al. |
| 4,540,586 A | 9/1985 | Moore |
| 4,564,627 A | 1/1986 | Hokazono et al. |
| 4,582,853 A | 4/1986 | Liu et al. |
| 4,598,097 A | 7/1986 | Perry et al. |
| 4,704,276 A | 11/1987 | Kantor |
| 4,735,735 A | 4/1988 | Borggrefe et al. |
| 4,735,809 A | 4/1988 | Donovan et al. |
| 4,738,852 A | 4/1988 | Watanabe et al. |
| 4,743,591 A | 5/1988 | Fukushima et al. |
| 4,746,531 A | 5/1988 | Lush |
| 4,754,047 A | 6/1988 | Kierman et al. |
| 4,792,546 A | 12/1988 | Baker |
| 4,794,105 A | 12/1988 | Hasegawa et al. |
| 4,876,097 A | 10/1989 | Autant et al. |
| 4,904,662 A | 2/1990 | Anderson et al. |
| 4,933,364 A | 6/1990 | Ivy et al. |
| 4,960,589 A | 10/1990 | Sasagawa |
| 4,970,080 A | 11/1990 | Laurent et al. |
| 4,971,826 A | 11/1990 | Kato et al. |
| 4,996,067 A | 2/1991 | Kobayashi et al. |
| 5,010,851 A | 4/1991 | Gvaryahu et al. |
| 5,021,241 A | 6/1991 | Yamahira et al. |
| 5,028,440 A | 7/1991 | Nissen |
| 5,064,665 A | 11/1991 | Klopsenstein et al. |
| 5,102,871 A | 4/1992 | Furukawa |
| 5,110,592 A | 5/1992 | Stitt |
| 5,128,127 A | 7/1992 | Beck |
| 5,134,125 A | 7/1992 | Hara et al. |
| 5,137,735 A | 8/1992 | Bignon |
| 5,139,777 A | 8/1992 | Ott et al. |
| 5,145,695 A | 9/1992 | Smith et al. |
| 5,190,775 A | 3/1993 | Klose |
| 5,208,034 A | 5/1993 | Herting et al. |
| 5,219,596 A | 6/1993 | Smith et al. |
| 5,236,718 A | 8/1993 | Huchette |
| 5,244,669 A | 9/1993 | Satoh et al. |
| 5,252,561 A | 10/1993 | Hornykiewytsch et al. |
| 5,264,417 A | 11/1993 | Okada et al. |
| 5,268,357 A | 12/1993 | Yabiki et al. |
| 5,292,721 A | 3/1994 | Boyd et al. |
| 5,296,243 A | 3/1994 | Lange et al. |
| 5,369,128 A | 11/1994 | Hsu |
| 5,380,525 A | 1/1995 | Leedle et al. |
| 5,420,163 A | 5/1995 | Potter et al. |
| 5,427,802 A | 6/1995 | Evans et al. |
| 5,431,928 A | 7/1995 | Saito et al. |
| 5,455,263 A | 10/1995 | Doscher et al. |
| 5,462,967 A | 10/1995 | Hayaski |
| 5,474,785 A | 12/1995 | Wright et al. |
| 5,480,659 A | 1/1996 | Tokach et al. |
| 5,496,571 A | 3/1996 | Blazdon et al. |
| 5,503,112 A | 4/1996 | Luhman et al. |
| 5,516,798 A | 5/1996 | Ferket |
| 5,518,730 A | 5/1996 | Fuisz |
| 5,529,793 A | 6/1996 | Garner et al. |
| 5,534,269 A | 7/1996 | Igari et al. |
| 5,547,686 A | 8/1996 | Jenkins |
| 5,560,919 A | 10/1996 | Morikawa et al. |
| 5,585,134 A | 12/1996 | Cummings et al. |
| 5,597,797 A | 1/1997 | Clark |
| 5,607,840 A | 3/1997 | Van Corp et al. |
| 5,624,686 A | 4/1997 | Shimoda et al. |
| 5,641,759 A | 6/1997 | Patterson et al. |
| 5,641,806 A | 6/1997 | Eisenbei et al. |
| 5,660,852 A | 8/1997 | McKeown et al. |
| 5,686,490 A | 11/1997 | Okazaki et al. |
| RE35,699 E | 12/1997 | Lange et al. |
| 5,707,617 A | 1/1998 | Conrad et al. |
| 5,741,489 A | 4/1998 | Pimentel |
| 5,741,506 A | 4/1998 | Bauchart et al. |
| 5,795,602 A | 8/1998 | Craig et al. |
| 5,807,594 A | 9/1998 | King et al. |
| 5,814,333 A | 9/1998 | Onishi et al. |
| 5,824,707 A | 10/1998 | Saxton |
| 5,840,332 A | 11/1998 | Lerner et al. |
| 5,843,498 A | 12/1998 | Takahashi |
| 5,858,424 A | 1/1999 | Virkki et al. |
| 5,871,802 A | 2/1999 | Gao et al. |
| 5,876,780 A | 3/1999 | Virtanen et al. |
| 5,882,685 A | 3/1999 | Ashmead |
| 5,906,842 A | 5/1999 | Sato et al. |
| 5,908,634 A | 6/1999 | Kemp et al. |
| 5,935,623 A | 8/1999 | Alonso-Debolt |
| 5,962,423 A | 10/1999 | Bundle et al. |
| 6,008,252 A | 12/1999 | Beale |
| 6,019,995 A | 2/2000 | Steensma |
| 6,039,874 A | 3/2000 | Teran et al. |
| 6,054,481 A | 4/2000 | Pageat |
| 6,086,878 A | 7/2000 | Adalsteinsson et al. |
| 6,117,458 A | 9/2000 | Morgan |
| 6,120,815 A | 9/2000 | Moore |
| 6,133,323 A | 10/2000 | Hayek |
| 6,162,473 A | 12/2000 | Fodge et al. |
| 6,168,803 B1 | 1/2001 | Harris |
| 6,183,769 B1 | 2/2001 | Campbell et al. |
| 6,199,512 B1 | 3/2001 | Jefferson et al. |
| 6,217,915 B1 | 4/2001 | Luchansky et al. |
| 6,224,872 B1 | 5/2001 | Shibuya et al. |
| 6,224,917 B1 | 5/2001 | Murto |
| 6,229,031 B1 | 5/2001 | Strohmaier et al. |
| 6,254,904 B1 | 7/2001 | Bailey |
| 6,291,435 B1 | 9/2001 | Yanmaele et al. |
| 6,306,427 B1 | 10/2001 | Annonier et al. |
| 6,326,051 B1 | 12/2001 | Nakasuai et al. |
| 6,414,035 B1 | 7/2002 | Vareas Munita et al. |
| 6,440,447 B1 * | 8/2002 | Luhman ............... A61K 31/045 |
| | | 424/438 |
| 6,451,360 B2 | 9/2002 | Bailey et al. |
| 6,866,861 B1 | 3/2005 | Luhman |
| 8,519,008 B2 * | 8/2013 | de Rodas ............... A01K 9/00 |
| | | 424/442 |
| 9,078,457 B2 * | 7/2015 | de Rodas ............... A01K 9/00 |
| 9,433,232 B2 * | 9/2016 | de Rodas ............... A01K 9/00 |
| 2001/0003592 A1 | 6/2001 | Sato et al. |
| 2001/0009668 A1 | 7/2001 | Richardson |
| 2002/0004096 A1 | 1/2002 | Shinzato et al. |
| 2002/0004192 A1 | 1/2002 | Lee et al. |
| 2002/0022049 A1 | 2/2002 | Allen et al. |
| 2002/0025325 A1 | 2/2002 | Chu et al. |
| 2002/0127259 A1 | 9/2002 | Orthoefer |
| 2003/0072788 A1 | 4/2003 | Luhman |

FOREIGN PATENT DOCUMENTS

| | | |
|---|---|---|
| EP | 0289186 | 11/1988 |
| EP | 0021230 | 7/1990 |
| EP | 0192360 | 12/1991 |
| EP | 0549478 | 6/1993 |
| EP | 0646325 | 4/1995 |
| EP | 0661004 | 7/1995 |
| EP | 0698347 | 2/1996 |
| EP | 0998853 | 5/2000 |
| EP | 1175907 | 1/2002 |
| EP | 1183952 | 3/2002 |
| GB | 0838766 | 6/1960 |
| GB | 2159690 | 11/1985 |
| JP | 10-295284 | 11/1998 |
| JP | 2000-300115 | 10/2000 |
| WO | WO 1985/01639 | 4/1985 |
| WO | WO 1988/04930 | 7/1988 |

(56) References Cited

FOREIGN PATENT DOCUMENTS

| | | |
|---|---|---|
| WO | WO 1989/10067 | 11/1989 |
| WO | WO 1991/06316 | 5/1991 |
| WO | WO 1992/12639 | 8/1992 |
| WO | WO 1993/02558 | 2/1993 |
| WO | WO 1993/16175 | 8/1993 |
| WO | WO 1993/21782 | 11/1993 |
| WO | WO 1994/17678 | 8/1994 |
| WO | WO 1994/22324 | 10/1994 |
| WO | WO 1996/12413 | 5/1996 |
| WO | WO 1997/00017 | 1/1997 |
| WO | WO 1997/33486 | 9/1997 |
| WO | WO 1997/33488 | 9/1997 |
| WO | WO 1999/00136 | 1/1999 |
| WO | WO 1999/41996 | 8/1999 |
| WO | WO 1999/52379 | 10/1999 |
| WO | WO 2000/69275 | 11/2000 |
| WO | WO 2000/76303 | 12/2000 |
| WO | WO 2000/78160 | 12/2000 |
| WO | WO 2001/10239 | 2/2001 |
| WO | WO 2001/67879 | 9/2001 |
| WO | WO 2001/89317 | 11/2001 |
| WO | WO 2001/95891 | 12/2001 |
| WO | WO 2002/09728 | 2/2002 |
| WO | WO 2002/24208 | 3/2002 |
| WO | WO 2003/037102 | 5/2003 |
| WO | WO 2003/045401 | 6/2003 |
| WO | WO 2003/090696 | 11/2003 |

OTHER PUBLICATIONS

H. Khalili et. al.; The Effects of Added Glycerol or Unprotected Free Fatty Acids or a Combination of the Two on Silage Intake, Milk Production, Rumen Fermentation and Diet Digestibility in Cows Given Grass Silage Based Diets; Agric. Food Sci. Finland; vol. 6; Nos. 5-6; No. 349-362; May 1997.

Remond, B, and Jacquier, Carole; Effet De L'addition De Sorbitol A La Ration Des Vaches Laitieres En Debut De Lactation Sur Leurs Performances et Sur Quelques Parametres Sanguins; Reprod Nutr. Dev. 26 (1 B); pp. 365-366; 1986. (Accompanied by English language translation—6 pages).

Makinen et al.; A Polyol Mixture in the Diet of Dairy Cows; Nutr. Rep. Int.; 23 (6); pp. 1077-1088; 1981.

Choung, Jai-Jun & Chamberlain, David; "The Effects of Abomasal Infusions of Casein or Soy-Bean-Protein Isolate on the Milk Production of Dairy Cows in Mid-Lactation;" pp. 103-115 (British Journal of Nutrition) 1993.

Abstract of Article entitled: "Abomasal Infusion of Glucose and Fat-Effect on Digestion, Production, and Ovarian and Uterine Functions of Cows" from 80: 1315-1328 of 1997 J. Dairy Sci;_ Abstract published at http://www.aces.uiuc.edu/~gregm/adsa/jds/abs/97/Jul97/ab1315.html and dated Jul. 1997.

Abstract (pp. 538-539, Journal of British Society of Animal Production) of: L. Istasse & E.R. Orskov, "The Effects of Abomasal Infusions of Casein or Glucose on Milk Yield and on Some Blood Constituents of Dairy Cows in early and Late Lactation."

Abstract (Proceedings of the Nutrition Society, p. 65A, vol. 43, 1984) of: J.D. Oldham & J.A. Bines, "Milk Production in Cows Infused Abomasally with Casein, Glucose or Aspartic and Glutamic Acids Early in Lactation."

Lister, Cliff J. and Smithard, Ronald R.; Effects of Intraruminal Administration of Polyol to Sheep; J. Sci. Food Agric. 1984, 35, pp. 21-28.

Sauer, F.D., Ertle, J.D., Fisher, LJ.; *Propylene Glycol and Glycerol As a Feed Additive for Lactating Dairy Cows: An Evaluation of Blood Metabolite Parameters*; Canadian Journal of Animal Science; vol. 53, pp. 265-271 (1973).

Fisher, L.J., Ertle, J.D., Lodge, G.A.; Sauer, F.D.; *Effects of Propylene Glycol or Glycerol Supplementation of the Diet of Dairy Cows On Feed Intake, Milk Yield and Composition, and Incidence of Ketosis*; Canadian Journal of Animal Science; vol. 53; pp. 289-296 (1973).

Ensminger, Animal Science 1977; pp. 714,736,737,744-747.

Trottier, N. L., C. F. Shipley and R. A. Easter. Plasma amino acid uptake by the mammary gland of the lactating sow J. Anim. Sci. 75:1266-1278.1997.

Stein, H. H., S. Aref, and R. A. Easter. Comparative protein and amino acid digestibilities in growing pigs and sows. J. Anim. Sci. 77: 1169-1179. 1999.

Stein, H. H., N. L. Trottier, C. Bellaver, and R. A. Easter. The effect of feeding level and physiological status on total flow and amino acid composition of endogenous protein at the distal ileum in swine. J. Anim. Sci. 77:1180-1187.

Kim, S. W., W. L. Hurley, I. K. Han, and R. A. Easter. Changes in tissue composition associated with mammary gland growth during lactation in the sow. J. Anim. Sci. 77:2510-2516. 1999.

Kim, S. W., W. L. Hurley, I. K. Han, H. H. Hans, and R. A. Easter. Effect of Nutrient Intake on Mammary Gland Growth in Lactating Sows. J. Anim. Sci. 77:3304-3315. 1999.

Kim, S. W., I. Osaka, W. L. Hurley, and R. A. Easter. Mammary Gland Growth as Affected by Litter Size in Lactating Sows: Impact on Lysine Requirement. J. Anim. Sci. 77:3316-3321. 1999.

Kim, S. W., D. H. Baker and R. A. Easter. Dynamic ideal protein and limiting amino acids for lactating sows: the impact of amino acid mobilization. J. Anim. Sci. 79:2356-2366. 2001.

Kim, S. W., M. Grossman and R. A. Easter. A dynamic simulation model to describe nutrient flow in lactating sows. J. Anim. Sci. 77 (Suppl. 1):181 (Abstr.). 1999.

Nielsen, T. T., N. L. Trottier, C. Bellaver, H. H. Hans, and R. A. Easter. Effect of litter size on mammary gland amino acid uptake in lactating sows. Livest. Prod. Sci. 50:167 (Abstr.). 1997.

Noble, M. S., M. B. Wheeler, and W. L. Hurley. Association of total milk solids and litter growth: data from αlactalbumin transgenic sows. in University of Illinois Swine Research Report, Dept. of Animal Sciences, University of Illinois, pp. 131-133.2001.

Management of the Nursery Pig by Ioannis Mavromichalis, M.Sc. (13 pages). 1999.

Dynamic Ideal Protein: A Novel Approach to Feeding Lactating Sows; Dpt. of Animal Sciences; University of Illinois at Urbana-Champaign; S.W. Kim, D.H. Baker and R.A. Easter; pp. 122-125. 2001.

* cited by examiner

METHODS FOR FEEDING SOWS AND FOR IMPROVING THE HEALTH OF YOUNG PIGLETS

CROSS-REFERENCED RELATED APPLICATIONS

This applications is a continuation of U.S. patent application Ser. No. 14/788,922 filed on Jul. 1, 2015, issued as U.S. Pat. No. 9,433,232 on Sep. 6, 2016, which is a continuation of U.S. patent application Ser. No. 13/973,486 filed on Aug. 22, 2013, issued as U.S. Pat. No. 9,078,457 on Jul. 14, 2015, which is a continuation of U.S. patent application Ser. No. 10/349,743 filed on Jan. 22, 2003, issued as U.S. Pat. No. 8,519,008 on Aug. 27, 2013, the entire contents of each are incorporated herein by reference.

BACKGROUND OF THE INVENTION

The present invention generally relates to a method and composition for feeding lactating monogastric mammals. More particularly, the present invention relates to a method and composition for improving the health, litter weight, and survival of young, monogastric mammals, such as nursing piglets.

The economic viability of a pork producer is directly related to the litters of the producer's sows. In particular, litter weights at weaning and the mortality rate of the litters are important factors. Over the past decade or so, advances in sow feeding techniques have caused litter sizes produced by sows to generally increase while generally decreasing the lactation periods of farrowing sows. Despite these improved litter results, mortality rates for piglet litters have not significantly dropped while overall litter weights at weaning have disappointingly remained stagnant.

Piglet mortality rates are typically highest during the first four days following piglet birth. Despite advances in sow feeding technology, litter mortality rates of piglets, as measured from birth to weaning, have continued to average around 12%, with the top ten pork producers averaging around 10.2% and the bottom ten producers averaging around 15.5%. This is troublesome for pork producers because the economic viability of their business is directly related to the overall number of piglets per litter that survive weaning and thereafter reach market weight.

Data from the National Animal Health Monitoring System (NAHMS, 2001; http://www.aphis.usda.gov/vs/ceah/cahm/Swine/swine.htm) indicate that about 10.9 piglets are born per sow per litter, on average. However, only about 10.0 piglets of each litter are alive at birth, and only about 8.9 piglets per litter survive at weaning. This translates to a pre-weaning mortality rate among piglet litters to be about 11.0%. Lay et al., 2001 (JAS, 2001). Starvation, low birth weight, sickness, hypothermia, and crushing or suffocation all contribute to this relatively high piglet mortality rate.

A larger litter weight at weaning often corresponds directly to how fast the piglets of the litter will grow to market weight. On the other hand, a smaller litter weight often means the litter has a higher percentage of low weight piglets that are more likely to die prior to weaning, as compared to their heavier brothers and sisters of the litter. For instance, lighter weight piglets are especially susceptible to hypothermia because of they have a larger ratio of surface area to body weight than heavier piglets. To counter this susceptibility to hypothermia, lighter weight piglets tend to lie more closely to the sow to obtain warmth, though such close proximity to the sow increases the chance the lighter weight piglets will be crushed or suffocated by the sow.

Additionally, lighter weight piglets typically have only a minimal amount of reserve energy stored at birth and therefore are at an increased risk of hypoglycemia (low blood sugar) shortly after birth if the lighter weight piglets do not receive adequate nourishment in the first few days following birth. Similarly, lighter weight piglets that are sick, injured, or out-competed at mealtime by heavier piglets of the litter may miss a feeding, become progressively weaker and therefore continue to miss subsequent feedings, and eventually starve to death. Thus it is increasingly important to pork producers to assure that all piglets of the litter, especially those with a relatively low birth weight and most at risk of dying, receive adequate caloric intake starting at birth to maximize piglet survival rates from each litter.

Although various feeding techniques have been proposed and/or practiced over the years and have enhanced the overall knowledge base with respect to swine feeding, these techniques have not adequately addressed the problem of how to most economically, efficiently, and effectively increase both the survival rate of young piglets at weaning and young piglet litter weights at weaning. The present invention provides a composition and method for feeding lactating sows that has been surprisingly found to significantly reduce mortality rates of nursing piglets, while increasing litter and young piglet weights at weaning.

BRIEF SUMMARY OF THE INVENTION

The present invention includes a method of improving the health of a group of young monogastric mammals where the group of young monogastric mammals is nursing from a lactating monogastric mammal during a pre-weaning period. The method entails feeding the lactating monogastric mammal an effective amount of an animal feed during the pre-weaning period, and feeding the lactating monogastric mammal an effective amount of sugar alcohol during the pre-weaning period. The present invention further includes a method of reducing the mortality rate of a group of young monogastric mammals, a method of increasing the weight gained by a group of young monogastric mammals during a pre-weaning period, and a lactating monogastric mammal ration.

DETAILED DESCRIPTION

The present invention generally relates to a method and composition for feeding lactating monogastric mammals. More particularly, the present invention relates to a method and composition for improving the health, such as the survival rate and litter weight, of young, monogastric mammals, such as nursing piglets. For example, the present invention includes methods and compositions for increasing the survival rate of nursing piglets at weaning, increasing live piglet litter weights at weaning, and increasing individual live piglet weights at weaning. The method of the present invention generally entails providing lactating sows with a feed composition that includes sugar alcohol, where the feed composition may, for example, be orally fed to the lactating sows.

It has been surprisingly discovered that if sugar alcohol is consumed by, or otherwise provided to, lactating, monogastric mammals, even at low rates, such as rates on the order of about five grams of sugar alcohol per day to about 100 grams per day, or even higher, as part of a feed composition, young monogastric mammals that are nursing from the lactating, monogastric mammals exhibit improved health, as compared to litters of the young monogastric mammals (i.e.: groups of the young monogastric mammals) that are nursing from lactating, monogastric mammals not receiving any sugar alcohol. For example, litters of the young monogastric mammals that are nursing from lactating, monogastric mammals that receive sugar alcohol in this fashion exhibit increased survival rates (i.e. decreased mortality rates), both over an entire pre-weaning period and over intermediate portions of the pre-weaning period, as compared to litters of the young monogastric mammals that are nursing from lactating, monogastric mammals not receiving any sugar alcohol.

Likewise, litters of the young monogastric mammals that are nursing from lactating, monogastric mammals that receive sugar alcohol in this fashion exhibit increased overall litter live weights (i.e. total weight of living young monogastric mammals), as compared to litters of the young monogastric mammals that are nursing from lactating, monogastric mammals not receiving any sugar alcohol. Furthermore, individual young monogastric mammals that are nursing from lactating, monogastric mammals that receive sugar alcohol in this fashion exhibit increased mean weights, as compared to individual young monogastric mammals that are nursing from lactating, monogastric mammals not receiving any sugar alcohol.

The inventors have observed other surprises while practicing the present invention. For example, despite yielding healthier young monogastric mammals with lower mortality rates, increased overall litter live weights, and/or increased mean individual weights during all or part of the pre-weaning period, lactating, monogastric mammals that receive sugar alcohol in this fashion while nursing the young monogastric mammals surprisingly show no significant changes in overall feed intake during the pre-weaning period, as compared to lactating, monogastric mammals not receiving any sugar alcohol while nursing young monogastric mammals. As another example, despite still yielding healthier young monogastric mammals with lower mortality rates, increased overall litter live weights, and/or increased mean individual weights during all or part of the pre weaning period, lactating, monogastric mammals that receive sugar alcohol in this fashion while nursing the young monogastric mammals surprisingly, though not necessarily desirably, show no significant changes in backfat thickness during the pre-weaning period, as compared to lactating, monogastric mammals not receiving any sugar alcohol while nursing young monogastric mammals.

The ability of lactating, monogastric mammals that receive sugar alcohol in accordance with the present invention, to yield healthier young monogastric mammals with lower mortality rates, increased overall litter live weights, and/or increased mean individual weights during all or part of the pre-weaning period, as compared to lactating, monogastric mammals that do not receive sugar alcohol in accordance with the present invention, while not significantly increasing either backfat thickness or feed intake, is believed to demonstrate an increase in milk production efficiency by the lactating, monogastric mammals that receive sugar alcohol in accordance with the present invention during the pre-weaning period. Even while achieving this increased milk production efficiency, the lactating, monogastric mammals that receive sugar alcohol in accordance with the present invention produce beneficial amounts of milk with a nutritional composition that is beneficial to the health of young monogastric mammals nursing from the lactating, monogastric mammals that receive the sugar alcohol.

As used herein, the term "milk production efficiency" means the ratio of the volume of milk produced by the lactating monogastric mammal, such as the lactating sow, versus the amount of feed consumed by the lactating monogastric mammal, such as the lactating sow, based on the dry weight of the feed. Preferably, lactating, monogastric mammals, such as lactating sows, that receive sugar alcohol in accordance with the present invention exhibit an increased milk production efficiency during the pre-weaning period, as compared to lactating, monogastric mammals, such as lactating sows, that do not receive sugar alcohol in accordance with the present invention. More preferably, lactating, monogastric mammals that receive sugar alcohol in accordance with the present invention exhibit at least about a two percent increased in milk production efficiency during the pre-weaning period, and more preferably at least about a four percent increase in milk production efficiency during the pre-weaning period, as compared to lactating, monogastric mammals that do not receive sugar alcohol in accordance with the present invention As used herein, the term "monogastric mammal" refers to mammals that have a stomach with only a single chamber. Monogastric mammals are different from, and therefore are distinguished from, ruminants. Ruminants are even-toed hoofed animals, such as cattle, sheep, goats, oxen, musk ox, llamas, alpacas, guanicos, deer, bison, antelopes, camels, and giraffes that have a complex 3- or 4-chamber stomach and typically re-chew what food material that has been previously swallowed. The single-chambered stomach of monogastric mammals causes digestion and nutrient assimilation to occur differently in monogastric animals, as compared to ruminants. Some non-exhaustive examples of monogastric mammals are swine, such as pigs and hogs; rats; mice; horses; rabbits; raccoons; dogs; cats; and humans. The present invention is believed applicable and beneficial to all monogastric mammals; therefore, the term monogastric mammal, as used herein, means all monogastric mammals, any individual example of any monogastric mammal, or any combination of different monogastric mammals.

Swine, such as pigs and hogs, are examples of monogastric mammals of particular interest to the present invention since the research culminating in the present invention was ultimately directed at increasing production of farm-based monogastric mammals for slaughter and swine are probably the best example of farm-based monogastric mammals that are raised for slaughter. Consequently, the present invention is generally described herein with reference to swine, such as pigs and hogs. Nonetheless, though the present invention is generally described in the context of swine, the present invention is believed equally applicable to any monogastric mammal, including, but not limited to swine, such as pigs and hogs; rats; mice; horses; rabbits; raccoons; dogs; cats; and humans, for purposes of achieving the described health benefits of the present invention.

Weaning of young, monogastric mammals occurs when the diet of the young monogastric animals is modified to include primarily solid animal feed, as opposed to liquid feed, such as sow's milk in the case of young piglets. Otherwise stated, young, monogastric mammals are considered to be weaned when the young, monogastric mammals are no longer allowed to nurse from any female monogastric mammal or is no longer primarily provide either natural liquid milk from any female monogastric mammal or artificial liquid milk that simulates natural liquid milk of any female monogastric mammal. For example, piglets are considered to be weaned when the piglets are no longer allowed to nurse from any sow and are not primarily provided either natural sow's milk or an artificial sow's milk that simulates natural sow's milk. Correspondingly, as used herein, the term "pre-weaning period" refers to the period when nutrients are primarily supplied to the young, monogastric mammals, such as piglets, in liquid form, as part of a liquid feed, and the term "post-weaning period" refers to the period when nutrients are no longer primarily provided to young, monogastric mammals, such as the piglets, in the form of liquid feed.

As used herein, the term "sugar alcohol" means a polyhydric alcohol formed by the reduction of the carbonyl group of a sugar to a carbon atom of the sugar alcohol. The sugar alcohol that may be employed when practicing the present invention may take any form. For example, the sugar alcohol may be employed as solid, crystalline, sugar alcohol; a sugar alcohol syrup; an aqueous mixture of water and crystalline sugar alcohol; a mixture of an edible organic solvent and crystalline sugar alcohol; an aqueous mixture of water and sugar alcohol syrup; and/or a mixture of an edible organic solvent and sugar alcohol syrup.

When the sugar alcohol is supplied as an aqueous mixture, the aqueous mixture may contain any concentration of sugar alcohol. Thus, some non-exhaustive examples of permissible aqueous sugar alcohol solutions are aqueous sugar alcohol solutions containing from about 5 weight percent sugar alcohol to about 99 weight percent sugar alcohol and more preferably from about 30 weight percent sugar alcohol to about 80 weight percent sugar alcohol, based on the total weight of the aqueous sugar alcohol solution. Still more preferably, the aqueous sugar alcohol solution contains up to about 70 weight percent sugar alcohol, based on the total weight of the aqueous sugar alcohol solution, since aqueous sugar alcohol solutions containing more than about 70 weight percent sugar alcohol tend to be fairly viscous solutions that are more difficult to dispense and measure at ambient temperatures of about 72° F., or lower. Even more preferably, the aqueous sugar alcohol solution contains from about 50 weight percent sugar alcohol to about 70 weight percent sugar alcohol, based on the total weight of the aqueous sugar alcohol solution, to reduce the amount of water added to the animal feed when incorporating the sugar alcohol in the feed composition. Most preferably, the aqueous sugar alcohol solution contains about 70 weight percent sugar alcohol, based on the total weight of the aqueous sugar alcohol solution, to further minimize the amount of water added to the animal feed when incorporating the sugar alcohol in the feed composition.

Some non-exhaustive examples sugar alcohols that may be employed as the sugar alcohol of the present invention include adonitol; allitol; altritol (D-altritol, L-altritol, and D,L altritol); arabinitol (D-arabinitol, L-arabinitol, and D,L arabinitol); dulcitol (a.k.a. galactitol); erythritol; galaxitol; glucitol (D-glucitol, L-glucitol, and D,L glucitol); glycerol; iditol (D-iditol and L-iditol); inositol; isomalt; lactitol; maltitol; mannitol (D-mannitol, L-mannitol, and D,L mannitol); perseitol; ribitol; rhamnitol; sorbitol; threitol (D-threitol, L-threitol, and D,L threitol); xylitol; and any combination of these or other sugar alcohols. One preferred example of the sugar alcohol that may be employed when practicing the present invention is sorbitol.

In addition to, or along with, the sugar alcohol, the feed composition that is provided to the lactating monogastric mammal, such as the lactating sow, may include any other conventional animal feed component that is capable of being blended with the sugar alcohol as part of the feed composition or that is capable of being combined with the feed composition of the present invention, so long as the feed component does not disrupt digestive function of the lactating monogastric mammal, is not otherwise harmful to the lactating monogastric mammal, and is not harmful to the young monogastric mammal nursing from the lactating monogastric mammal vis a vis the milk supplied from the lactating monogastric mammal to the young monogastric mammal. Where the monogastric mammal is swine, some non-exhaustive examples of such conventional animal feed components that may be included as part of the feed composition of the present invention include water; processed grains, such as ground corn, soybean meal, and any combination of these or other processed grains; a high protein meal derived from any suitable animal or marine source; feed-grade tallow; any grease, such as white grease or yellow grease, hydrolyzed fat from any animal or plant source; commercially available formula feeds; and any mixture of any of these animal feed components that results in an animal feed that meets the nutritional requirements of the lactating swine.

Some examples of suitable formula feeds where the lactating monogastric mammal is a lactating sow include the Litter Max® line of swine lactation feeds that from available from Land O'Lakes Farmland Feed LLC of Arden Hills, Minn. For example, Litter Max® HML Premix may be employed as a component of the feed composition of the present invention as a formula feed. Litter Max® HML Premix contains vitamins and minerals that support enhanced gestation and lactation performance in sows. A variety of other premixes, such as inhibitor premixes, enzyme premixes, vitamin premixes, trace mineral premixes, and any combination of any of these premixes may also be included in the animal feed that is employed in the present invention. One exemplary inhibitor premix is Micro-Aid® premix that is available from Canadian Bio-Systems Inc. of Calgary, Alberta, Canada. Micro-Aid® premix inhibits the urease enzyme and thereby reduces release of ammonia from urea in fecal material produced by the swine.

Where the lactating monogastric mammal is a lactating sow, the animal feed may generally contain about ten to about thirty weight percent crude protein, preferably contains about fourteen to about twenty weight percent crude protein, and more preferably contains about sixteen weight percent crude protein, based on the total dry weight of the animal feed (excluding the dry weight of the sugar alcohol). Where the lactating monogastric mammal is a lactating sow, the animal feed may generally contain from zero to about ten weight percent crude fat, preferably contains about two to about four weight percent fat, and more preferably contains about 2.8 weight percent crude fat, based on the total dry weight of the animal feed (excluding the dry weight of the sugar alcohol). One preferred formulation of the animal feed, where the lactating monogastric mammal is a lactating sow, includes about 63.9 weight percent ground corn, about 28.65 weight percent soybean meal, about 5 weight percent of the Litter® HML Premix, about 2.3 weight percent choice white grease, and about 0.10 weight percent Micro-Aid® premix, based upon the dry matter weight of the feed composition (excluding the dry weight of the sugar alcohol).

Collectively, the animal feed and the sugar alcohol form the feed composition. The animal feed that is provided in combination with the sugar alcohol may be provided to the lactating monogastric mammal in any conventional fashion, but is preferably orally fed to the lactating monogastric mammal. Likewise, the sugar alcohol may be provided to the lactating monogastric mammal in any conventional fashion, but is preferably orally fed to the lactating monogastric mammal. For example, the sugar alcohol may in the form of solid sugar alcohol crystals that are physically mixed with other components of the feed composition. As another alternative, the sugar alcohol may be physically bound within another component of the feed composition, as in an extruded nugget that contains the sugar alcohol along with, for example, grain-based meal(s) of the feed composition. As yet another alternative, a liquid form of the sugar alcohol may be applied onto all or a portion of the animal feed and thereafter mixed with the animal feed or with the portion of the animal feed.

Applying a liquid form of the sugar alcohol onto a portion of the animal feed and thereafter mixing the applied liquid with the animal feed composition is one preferred technique for incorporating the sugar alcohol into the feed composition. According to this technique, an aqueous solution of the sugar alcohol that preferably contains at least about thirty weight percent sugar alcohol, based upon the total weight of the mixture, is heated to an application temperature. The application temperature is preferably warm enough to allow the aqueous solution of the sugar alcohol to be easily applied onto the portion of the animal feed by the chosen application technique. The application temperature is preferably in the range of about 100° F. to about 120° F.

The warm aqueous sugar alcohol solution may then be applied to the animal feed portion in any conventional fashion that is effective to coat the animal feed portion with the warm aqueous sugar alcohol solution, such as spraying the warm aqueous sugar alcohol solution onto the animal feed portion, brushing the warm aqueous sugar alcohol solution onto the animal feed portion, dipping the animal feed portion in the warm aqueous sugar alcohol solution, tumbling the animal feed portion with the warm aqueous sugar alcohol solution, or any combination of these. Preferably the warm aqueous sugar alcohol solution is sprayed onto the animal feed portion using a conventional hand-held sprayer. The animal feed portion coated with the warm aqueous sugar alcohol solution may then optionally be tumbled and mixed to more uniformly distribute the warm aqueous sugar alcohol solution. Thereafter, either with or without the optional tumbling and mixing step, the sugar-alcohol-coated animal feed portion (subsequently referred to as the "top-dressed animal feed portion" is preferably allowed to dry before the top-dressed animal feed portion is provided to the lactating monogastric mammal, such as the lactating sows. In one preferred example, the top-dressed animal feed portion is merely placed on top of the remainder of the animal feed provided to the lactating monogastric mammal for a particular feeding so the animal feed portion (top-dressed animal feed portion and the remainder of the animal feed portion) collectively contains the sugar alcohol dosage to be consumed by the lactating monogastric mammal during the particular feeding.

The sugar alcohol that is provided to the lactating monogastric mammal will typically be provided starting on the day when the young monogastric mammals are nursing from the lactating monogastric mammal and ending when the young monogastric mammals are no longer nursing from the lactating monogastric mammal (i.e. during the weaning period). The sugar alcohol dosage provided to the lactating monogastric mammal may be provided in any number of periodic increments to the lactating monogastric mammal that collectively equal the sugar alcohol dosage, with the caveat that the sugar alcohol dosage should preferably be provided to the lactating monogastric mammal on a daily basis as a daily sugar alcohol dosage. Also, each sugar alcohol dosage preferably contains at least about the same amount of sugar alcohol. Preferably, when the sugar alcohol is provided as a daily sugar alcohol dosage, the daily sugar alcohol dosage is divided into two increments that collectively equal the daily sugar alcohol dosage.

Though subsequent references to sugar alcohol dosages are provided primarily in terms of daily sugar alcohol dosages, it is to be understood that sugar alcohol dosages provided to the lactating monogastric mammals at other intervals, such as every other day or every third day, that attain the benefits of the present invention are considered to be within the scope of the present invention. Also, though the amount of sugar alcohol provided to the lactating monogastric mammals is stated on a daily basis, those of ordinary skill in the art will understand the amount of sugar alcohol provided on a daily basis will need to be converted to reflect any other sugar alcohol dosage interval; for example, where a daily sugar alcohol dosage of about 26 grams per day is employed, the sugar alcohol dosage, when provided on an every other day basis, would be about 52 grams per every other day, and the sugar alcohol dosage, when provided on an every third day basis, would be about 78 grams per every third day.

Any dosage of sugar alcohol may be provided to lactating monogastric mammals in accordance with the present invention. The sugar alcohol dosage provided to the lactating monogastric mammals preferably includes an amount of sugar alcohol that is effective (i.e. an effective amount) to improve at least one health characteristic of young monogastric mammals that are nursing from the lactating monogastric mammal receiving the sugar alcohol dosage, as compared to that (those) health characteristic(s) of young monogastric mammals that are nursing from lactating monogastric mammal not receiving the sugar alcohol dosage. In the context of piglets, and equally applicable to any young monogastric mammals other than piglets, some non-exhaustive examples of such health characteristics include: increased mean weight gain by individual piglets of the litter during any portion of the pre-weaning period after the onset of nursing, increased mean weight gain by individual piglets of the litter at weaning (i.e.: during the entire pre-weaning period), increased overall live weight gain by a litter of piglets during any portion of the pre-weaning period after the onset of nursing, increased overall live weight gain by a litter of piglets at weaning (i.e. during the entire pre-weaning period), a decreased mortality rate among a litter of piglets as measured during any portion of the pre-weaning period after the onset of nursing, and a decreased mortality rate among a litter of piglets as measured over the entire pre-weaning period at the completion of weaning.

The amount of the animal feed provided to the lactating monogastric mammals in combination with the concentration of the sugar alcohol (i.e. the sugar alcohol dosage) incorporated in the animal feed composition in accordance with the present invention is preferably effective (i.e. an effective amount) to support improvement of at least one health characteristic of young monogastric mammals that are nursing from the lactating monogastric mammal receiving the sugar alcohol, as compared to that (those) health characteristic(s) of young monogastric mammals that are nursing from lactating monogastric mammal not receiving the sugar alcohol. Typically, and permissibly, the concentration of the sugar alcohol in the feed composition that is fed to the lactating monogastric mammal, such as the lactating sow, may range from about 0.1 weight percent to about 10 weight percent, based on the total dry weight of the feed composition, for purposes of achieving one or more improved health characteristics of young monogastric mammals, such as piglets, that are nursing from the lactating monogastric mammal, such as the lactating sow, that is receiving feed composition.

Some non-exhaustive examples of daily sugar alcohol dosage rates that are believed to be effective to improve at least one health characteristic of young monogastric mammals, such as piglets, that are nursing from the lactating monogastric mammal, such as the lactating sow, that is receiving the daily sugar alcohol dosage, as compared to that (those) health characteristic(s) of young monogastric mammals, such as piglets, that are nursing from another lactating monogastric mammal, such as another lactating sow, that is not receiving the daily sugar alcohol dosage are daily sugar alcohol dosage rates ranging from about five grams of sugar alcohol per day to about 200 grams per day, or more. Two exemplary daily sugar alcohol dosage rates within this range that are effective to improve at least one health characteristic of piglets that are nursing from the lactating sow that is receiving the daily sugar alcohol dosage, as compared to that (those) health characteristic(s) of piglets that are nursing from a lactating sow not receiving the daily sugar alcohol dosage are a daily sugar alcohol dosage rate of about 25 grams of sugar alcohol per day and a daily sugar alcohol dosage of about 50 grams per day, such as sugar alcohol dosage rates of 26 and 52 grams per day, respectively.

Any amount of the animal feed may be provided to the lactating monogastric mammals in combination with the sugar alcohol dosage to make up the feed composition in accordance with the present invention. The amount of the animal feed provided to the lactating monogastric mammals in combination with the sugar alcohol dosage in accordance with the present invention is preferably effective (i.e. an effective amount) to support improvement of at least one health characteristic of young monogastric mammals that are nursing from the lactating monogastric mammal receiving the sugar alcohol dosage, as compared to that (those) health characteristic(s) of young monogastric mammals that are nursing from lactating monogastric mammal not receiving the sugar alcohol dosage.

As one non-exhaustive example of suitable animal feed amounts for lactating sows, the animal feed may be provided to the lactating monogastric mammals, such as the lactating sows, at the rate of about four pounds per day for the first twenty-four hours post-farrowing, at the rate of about eight pounds per day for the second twenty-four hour period post-farrowing (i.e. from twenty-four hours post-farrowing to forty-eight hours post-farrowing), at the rate of about twelve pounds per day for the third twenty-four hour period post-farrowing (i.e. from forty-eight hours post-farrowing to seventy-two hours post-farrowing), and ad libitum after the first seventy-two hours post-farrowing through the day of piglet weaning. The animal feed may permissibly be provided to the lactating monogastric mammals, such as the lactating sows, at any rate, including ad libitum, during the first seventy-two hours post-farrowing. Preferably, however, the animal feed is provided to the lactating monogastric mammals, such as the lactating sows, at a reduced rate that mimics the normal feed intake pattern of the lactating monogastric mammals during the first seventy-two hours post-farrowing to minimize waste of animal feed not consumed by the lactating monogastric mammals during the first seventy-two hours post-farrowing when the appetite of the lactating monogastric mammals is typically somewhat lower that normal due to the normal recovery from the farrowing event.

As used herein, unless otherwise indicated, any reference to "first," "second," "third," etc., when used in combination with "lactating mammal," "group of young mammals," "lactating sow," and "litter of piglets" is provided for purposes of distinguishing between different lactating mammals, between different groups of young mammals, between different lactating sows, and between different litters of piglets, and is not used as a reference to the number of litters or groups of young mammals delivered (birthed) by any particular lactating mammal or to the number of litters or groups of piglets delivered (birthed or farrowed) by any particular lactating sow.

The effective amount of the sugar alcohol may be considered in a comparison of a first lactating sow with a second lactating sow during a pre-weaning period, where the first lactating sow is fed the effective amount of the sugar alcohol in combination with the effective amount of the animal feed, a first litter of piglets is nursing from the first lactating sow, and a second litter of piglets is nursing from the second lactating sow. When used in combination with the effective amount of the sugar alcohol, the effective amount of the animal feed is the amount of the animal feed that is fed to the first lactating sow during the time period when the sugar alcohol is fed to the first lactating sow. When the effective amount of the animal feed is used in combination with the effective amount of the sugar alcohol, the animal feed and the sugar alcohol are preferably fed to the first lactating sow together as the feed composition.

When used in combination with the effective amount of the sugar alcohol, the animal feed is preferably fed to the first lactating sow ad libitum after the first seventy-two hours post farrowing, at a rate of about three to about five pounds per day (as is basis) during the first twenty-four hours post-farrowing, at a rate of about seven to about nine pounds per day (as is basis) during the second twenty-four hour period post-farrowing, and at a rate of about eleven to about thirteen pounds per day (as is basis) during the third twenty-four hour period post-farrowing. More preferably, in combination with the effective amount of the sugar alcohol, the animal feed is fed to the first lactating sow ad libitum after the first seventy-two hours post farrowing, at a rate of about four pounds per day (as is basis) during the first twenty-four hours post-farrowing, at a rate of about eight pounds per day (as is basis) during the second twenty-four hour period post-farrowing, and at a rate of about twelve pounds per day (as is basis) during the third twenty-four hour period post-farrowing.

Taking these considerations into account, the term "effective amount of the sugar alcohol," as used herein, means an amount of the sugar alcohol that, when fed during the pre-weaning period along with the effective amount of the animal feed to the first lactating sow that:
  (1) is preferably fed an equal amount of the same, or substantially the same, animal feed as that fed to the second lactating sow,
  (2) where the second lactating sow does not receive the effective amount of the sugar alcohol and preferably does not receive any sugar alcohol, and
  (3) while the first lactating sow and the second lactating sow also have equal access to water ad libitum,
is effective to cause at least one, preferably at least two, more preferably at least three, still more preferably at least four, even more preferably at least five, yet even more preferably at least six, yet still more preferably at least seven, even still more preferably at least eight, and most preferably all nine of the following improvements that are listed in (a), (b), (c), (d), (c), (e), (f), (g), (h), and (i) below:
  (a) an increased mean weight gain by individual piglets of the first litter of piglets during a portion of the pre-weaning period, as compared to the mean weight gain by individual piglets of the second litter of piglets during the portion of the pre-weaning period;

(b) an increased mean weight gain by individual piglets of the first litter of piglets at weaning (i.e. over the entire, or essentially the entire, pre-weaning period), as compared to the mean weight gain by individual piglets of the second litter of piglets at weaning (i.e. over the entire, or essentially the entire, pre-weaning period);

(c) an increased overall litter live weight gain by the first litter of piglets during a portion of the pre-weaning period, as compared to the overall litter live weight gain by the second litter of piglets during the portion of the pre-weaning period;

(d) an increased overall litter live weight gain by the first litter of piglets at weaning (i.e. over the entire, or essentially the entire, pre-weaning period), as compared to the overall litter live weight gain by the second litter of piglets at weaning (i.e. over the entire, or essentially the entire, pre-weaning period);

(e) a decrease in the mortality rate among the first litter of piglets to about 4.6 percent, or less, and preferably to about 4 percent, or less, during a portion of the pre-weaning period;

(f) a decrease in the mortality rate among the first litter of piglets to about 4.6 percent, or less, and preferably to about 5.7 percent, or less, at weaning (i.e. over the entire pre-weaning period);

(g) a decrease in the mortality rate among the first litter of piglets during a portion of the pre-weaning period, as compared to the mortality rate among the second litter of piglets during the portion of the pre-weaning period;

(h) a decrease in the mortality rate among the first litter of piglets at weaning (i.e. over the entire pre-weaning period), as compared to the mortality rate among the second litter of piglets at weaning (i.e. over the entire pre-weaning period); and (i) an increase in the milk production efficiency of the first lactating sow versus the milk production efficiency of the second lactating sow during all, or at least a portion, of the pre-weaning period.

Unless otherwise indicated herein, statements referring to the "effective amount of the sugar alcohol" are equally applicable to the "effective concentration of the sugar alcohol," where the concentration of the sugar alcohol refers to the concentration of the sugar alcohol in the feed composition, based on the total dry weight of the feed composition, and feed composition includes the animal feed and the sugar alcohol.

Despite improving the health of the first litter of piglets, the effective amount of the sugar alcohol, in combination with the effective amount of the animal feed, when consumed by a first lactating sow, does not cause any substantial change in animal feed intake, over the pre-weaning period as measured from start to finish of the pre-weaning period, as compared to the animal feed intake of a second lactating sow that is preferably on a diet that includes the animal feed, but is free of the effective amount of the sugar alcohol and preferably is free of any sugar alcohol. Also, despite improving the health of the first litter of piglets, the effective amount of the sugar alcohol, in combination with the effective amount of the animal feed, when consumed by a first lactating sow, does not cause any substantial change in backfat thickness, over the pre-weaning period as measured from start to finish of the pre-weaning period, as compared to the backfat thickness of a second lactating sow that is preferably on a diet that includes the animal feed, but is free of the effective amount of the sugar alcohol and preferably is free of any sugar alcohol.

The effective amount of the sugar alcohol, in combination with the effective amount of the animal feed, is preferably sufficient to decrease the mortality rate among the first litter of piglets during a portion of the pre-weaning period by at least about two percentage points, more preferably at least about four percentage points, still more preferably at least about five percentage points, even more preferably by at least about six percentage points, and yet more preferably by at least about eight percentage points, as compared to the mortality rate among the second litter of piglets during the portion of the pre-weaning period, where the second lactating sow is preferably on a diet that includes the animal feed, but is free of the effective amount of the sugar alcohol and preferably is free of any sugar alcohol.

Also, the effective amount of the sugar alcohol, in combination with the effective amount of the animal feed, is preferably sufficient to decrease the mortality rate among the first litter of piglets over the entire pre-weaning period by at least about two percentage points, more preferably at least about four percentage points, still more preferably by at least about five percentage points, and yet more preferably by at least about seven percentage points, as compared to the mortality rate among the second litter of piglets over the entire pre-weaning period, where the second lactating sow is preferably on a diet that includes the animal feed, but is free of the effective amount of the sugar alcohol and preferably is free of any sugar alcohol.

Additionally, the effective amount of the sugar alcohol, in combination with the effective amount of the animal feed, is preferably sufficient to decrease the mortality rate among the first litter of piglets over a portion of the pre-weaning period by at least about ten percent, preferably at least about twenty-five percent, more preferably at least about forty-eight percent, still more preferably at least about fifty-five percent, still more preferably by at least about sixty-seven percent, and yet more preferably by about one hundred percent, as compared to the mortality rate among the second litter of piglets during the portion of the pre-weaning period, where the second lactating sow is preferably on a diet that includes the animal feed, but is free of the effective amount of the sugar alcohol and preferably is free of any sugar alcohol.

Next, the effective amount of the sugar alcohol, in combination with the effective amount of the animal feed, is preferably sufficient to decrease the mortality rate among the first litter of piglets over the entire pre-weaning period by at least about ten percent, preferably at least about twenty-five percent, more preferably at least about forty-five percent, still more preferably at least about forty-eight percent, and still more preferably at least about fifty-seven percent, as compared to the mortality rate among the second litter of piglets over the entire pre-entire pre-weaning period, where the second lactating sow is preferably on a diet that includes the animal feed, but is free of the effective amount of the sugar alcohol and preferably is free of any sugar alcohol.

Finally, the effective amount of the sugar alcohol, in combination with the effective amount of the animal feed, is preferably sufficient to increase the overall litter live weight of the first litter of piglets over the entire pre-weaning period by at least about five percent, preferably at least about ten percent, more preferably at least about twelve percent, still more preferably at least about fourteen percent, and yet more preferably by at least about seventeen percent, as compared to the overall litter live weight of the second litter of piglets over the entire pre-weaning period, where the second lactating sow is preferably on a diet that includes the animal feed, but is free of the effective amount of the sugar alcohol and preferably is free of any sugar alcohol.

For these comparisons of the first lactating sow, first litter of piglets, second lactating sow, and second litter of piglets that are provided above in regard to the effective amount of the sugar alcohol and the effective amount of the animal feed, the first lactating sow and the second lactating sow may be provided with different animal feed, but are preferably provided with substantially the same animal feed, and are more preferably provided with the same animal feed. Furthermore, in these comparisons of the first lactating sow, the first litter of piglets, the second lactating sow, and the second litter of piglets that are provided above in regard to the effective amount of the sugar alcohol and the effective amount of the animal feed, the first lactating sow and the second lactating sow are preferably provided equal access to the animal feed and equal access to water ad libitum.

Though these comparisons that are provided above in regard to the effective amount of the sugar alcohol and the effective amount of the animal feed are provided in terms of a first lactating sow and a second lactating sow, these comparisons are equally applicable to a first group of lactating sows versus a second group of lactating sows, respectively. In this comparison of groups of lactating sows, the first group of lactating sows and the second group of lactating sows preferably include about the same number of lactating sows, preferably include the same or similar species (or the same or about the same weighting of different species), and preferably each include lactating sows with the same, or about the same, median age and with the same or a similar range of parities.

Various analytical techniques are employed herein. An explanation of these techniques follows. All values presented in this document for a particular parameter, such as weight percent total protein, weight percent fat, and weight percent total solids, are based on the "as is" sample and are therefore on a "wet basis", unless otherwise specified herein.
Property Determination and Characterization Techniques To determine the dry matter weight (or dry matter basis or dry basis) of a particular sample, the sample is first weighed. The weighed sample is then dried in an oven at a temperature that is adequate to drive off moisture from the sample without degrading the sample components, such as a temperature ranging from about 100° C. to about 110° C. The oven drying is continued until the weight of the dried sample remains constant, despite additional oven drying.

To determine the weight percent total solids, wet basis, in a sample, the actual weight of total solids is determined by analyzing the sample in accordance with Method #925.23 (33.2.09) of *Official Methods of Analysis*, Association of Official Analytical Chemists (AOAC) (16th Ed., 1995). The weight percent total solids, wet basis, is then calculated by dividing the actual weight of total solids by the actual weight of the sample.

To determine the weight percent total protein (crude protein), wet basis, in a sample, the actual weight of total protein is determined in accordance with Method #991.20 (33.2.11) of *Official Methods of Analysis*, Association of Official Analytical Chemists (AOAC) (16th Ed., 1995). The value determined by the above method yields "total Kjeldahl nitrogen," which is equivalent to "total protein" since the above method incorporates a factor that accounts for the average amount of nitrogen in protein. Since any and all total Kjeldahl nitrogen determinations presented herein are based on the above method, the terms "total Kjeldahl nitrogen" and "total protein" are used interchangeably herein. Furthermore, those skilled in the art will recognize that the term "total Kjeldahl nitrogen" is generally used in the art to mean "total protein" with the understanding the factor has been applied. The weight percent total protein, wet basis, is calculated by dividing the actual weight of total protein by the actual weight of the sample.

To determine the weight percent crude fat, wet basis, in a sample, the actual weight of fat in the sample is determined in accordance with Method #974.09 (33.7.18) of *Official Methods of Analysis*, Association of Official Analytical Chemists (AOAC) (16th Ed., 1995). The weight percent fat, wet basis, is then calculated by dividing the actual weight of fat in the sample by the actual weight of the sample.

The present invention is more particularly described in the following examples which are intended as illustrations only since numerous modifications and variations within the scope of the present invention will be apparent to those skilled in the art.

EXAMPLES

The examples provided below demonstrate the effect, during the pre-weaning period, of feeding lactating monogastric mammals, generally, and lactating sows, specifically, a control feed in combination with a sugar alcohol, such as sorbitol, as compared to the effect of feeding lactating monogastric mammals, generally, and lactating sows, specifically, the control feed in the absence of any sugar alcohol. In these examples, statistical analysis is provided for comparing the results of feeding the lactating sows the control feed in combination with sugar alcohol versus the results of feeding the lactating sows the control feed in the absence of sugar alcohol. Each lactating sow and each piglet included in these examples received routine care and management consistent with appropriate recommendations in the *Guide for the Care and Use of Agricultural Animals in Agricultural Research and Teaching* (1st edition, March 1988).

In each of the Examples provided below, each piglet was weighed two days after birth, fourteen days after birth, and again at weaning. All data that is provided in Tables 4-9 below for the lactating sows is based upon individual data for each lactating sow, then-present, as least square means of the particular data over all lactating sows present in the test at the time the particular data was recorded. All data that is provided in Tables 4-9 below for the piglets is based upon data for each litter of piglets, then-present, as least square means of the particular data over all piglets of the litter present in the test at the time the particular data was recorded. Data for parameters presented in Tables 4-9 was analyzed using the general linear model (GLM) statistical procedure of SAS™ statistical analysis software for a randomized complete block design that included both the particular feed regimen and the week of the test period in the model statement. The SAS™ statistical analysis software is available from SAS Institute, Inc. of Cary, N.C. Additionally, all data was analyzed to determine the mean of the data for each variable under consideration during the collection period for the particular data.

Additionally, the PDiff function of the GLM statistical procedure was used to characterize the mean values of the data by providing for comparisons between mean data values for the piglets or lactating sows of different treatments for particular test parameters or variables. The probability value P is a measure of the statistical probability that the differing parameter values derived from (1) lactating sows fed sugar alcohol versus (2) lactating sows not fed any sugar alcohol may be explained by the difference between receiving sugar alcohol and not receiving sugar alcohol.

A P value of 0.05 means that five times out of 100 the results can be explained by factors other than differences between the different treatments. Likewise, a P value of 0.77 means that 77 times out of 100, the difference in value between the control group fed only the control feed and the group fed the control feed and sugar alcohol may be explained by factors other than the differing feeding regimens. For purposes of comparing data in this document, P values of 0.10, or lower, are considered to be statistically significant. Thus, where a P value of 0.10 or less is returned for a particular variable, it is assumed the differing results are fully explained by the test regimen, i.e.: the presence or lack of the sugar alcohol in the diet of the particular lactating sow(s).

Also, many of Tables 4-9 include a coefficient of variation for data in a particular row. A coefficient of variation is simply the standard deviation of a particular variable that is divided by the mean of the variable and then multiplied by 100. Because variances and standard deviations are used to measure error, and because these values for variances and standard deviations are sensitive to the absolute scale of the variable, coefficients of variations are provided, since coefficients of variation remove the influence of the overall magnitude of the data.

In each of the Examples below, the control feed had the composition set forth in Table 1 below and the nutrient composition set forth in Table 2 below:

TABLE 1

Control Diet Ingredient Composition

| Ingredient | Concentration[a] (weight percent) |
|---|---|
| Ground Corn | 63.95 |
| High Protein Soybean Meal | 28.65 |
| LitterMax ® HML Premix | 5.00 |
| Choice White Grease | 2.30 |
| Micro-Aid Premix | 0.10 |

[a]Based on the total weight of the Control Diet

TABLE 2

Control Diet Nutrient Composition

| Nutritional Parameters | Value |
|---|---|
| Metabolizable Energy (Kcal/lb) | 1525 |
| Crude Fat (weight percent)[a] | 2.798 |
| Crude Protein (weight percent)[a] | 18.8 |
| Lysine (weight percent)[a] | 1.00 |
| Methionine (weight percent)[a] | 0.306 |
| Cysteine + Methionine (weight percent)[a] | 0.632 |
| Threonine (weight percent)[a] | 0.734 |
| Tryptophan (weight percent)[a] | 0.232 |
| Valine (weight percent)[a] | 0.887 |
| Calcium (weight percent)[a] | 1.000 |
| Phosphorus (weight percent)[a] | 0.800 |

[a]Based on the total weight of the Control Diet

The lactating sows were held in individual crates in a conventional farrowing facility and were individually fed. Each crate had wire flooring, a nipple water drinker, and a feeder. The sows in each crate had ad libitum access to water at all times.

For each individual lactating sow, the amount of the control feed consumed by the individual lactating sow was determined and recorded once daily by subtracting the weight of the control feed remaining at the end of the last daily feeding in the crate of the individual lactating sow from the total weight of control feed provided to the individual lactating sow during the three (morning, noon, afternoon) individual daily feed additions to the feed container of the individual lactating sow.

Example 1

In this example, sixty-two (62) lactating sows were subjected to one of three different feeding trials that each began shortly (within 48 hours) after the lactating sows gave birth to piglets (i.e.: shortly after farrowing) and extended to the day the different piglets were weaned from the respective sows. The purpose of this example was to evaluate the effect of feeding lactating sows varying amounts of sugar alcohol, or no sugar alcohol, on subsequent piglet litter performance parameters, such as mortality prior to weaning and litter weight gain during the pre-weaning period. Sorbitol was used as the sugar alcohol in this example.

Immediately after farrowing, twenty sows were randomly assigned to the Control, twenty-one sows were randomly assigned to Trial A, and twenty-one sows were randomly assigned to Trial B. Sow assignment did take into account parity (number of litters per sow) to artificially balance parity across the Control, Trial A, and Trial B. The different sows of the Control, Trial A, and Trial B had parities ranging from one to more than two. Additionally, litter size was equalized between the different sows of the Control, Trial A, and Trial B within forty-eight hours after farrowing to assure that all sows, whether assigned to the Control, Trial A or Trial B, had the same, or about the same, number of nursing piglets. The reason for waiting forty-eight hours before cross-fostering in this fashion was to assure each piglet received colostrum from their original dam.

In the Control, each of the twenty lactating sows were fed the control feed throughout the lactation period, where the control feed did not include any sugar alcohol. In Trial A, each of the lactating sows received the control feed plus about twenty-six grams of sorbitol per day. In Trial B, each of the lactating sows received the control feed plus about fifty-two grams of sorbitol per day.

The lactating sows of both Trial A and Trial B received the same daily amount of control feed that was fed to the lactating sows of the Control with the exception that two pounds of the control feed provided daily to the lactating sows of both Trial A and Trial B were replaced with two pounds of a sorbitol-coated control feed (hereinafter referred to as "top-dressed control feed"). To create the top-dressed control feed, liquid sorbitol was heated to a temperature ranging from about 100° F. and about 120° F. The heated liquid sorbitol was then sprayed over a batch of about three hundred to four hundred pounds of the control feed and thoroughly mixed to form the top-dressed control feed. Following mixing, the top-dressed control feed was divided and separately bagged in two pound increments. An appropriate ratio of the liquid sorbitol to the control feed was selected for the top-dressed control feed destined for the Trial A lactating sows to assure that each two pound allotment of the control feed destined for the Trial A lactating sows included about twenty-six grams of sorbitol. Likewise, an appropriate ratio of the liquid sorbitol to the control feed was selected for the top-dressed control feed destined for the Trial B lactating sows to assure that each two pound allotment of the top-dressed control feed destined for the Trial B lactating sows included about fifty-two grams of sorbitol.

During the feeding trial of this example, the top dressed control feed was applied three times daily to the balance of the control feed being provided individually at that feeding to the individual lactating sows of Trial A and Trial B. Approximately one-third of the top-dressed control feed was provided to the sows in the morning feeding, approximately one-third of the top dressed control feed was provided to the lactating sows in the noon feeding, and the remaining approximate one-third of the top-dressed control feed was provided to the sows in the afternoon feeding. The twenty-one sows of Trial A each received a total of about two pounds of the top-dressed control feed containing about 26 grams of sorbitol per day. The twenty-one sows of Trial B each received a total of about two pounds of the top-dressed control feed containing about 52 grams of sorbitol per day.

All sixty-two lactating sows of the Control, Trial A, and Trial B were offered a maximum of four (4) pounds of the control feed during the first twenty-four (24) hours after farrowing, a maximum of eight (8) pounds of the control feed during the second day (24 hours to 48 hours) after farrowing, and a maximum of twelve (12) pounds of the control feed during the third day (48 hours to 72 hours) after farrowing to mimic typical feeding patters of lactating sows during the first seventy-two hours post-farrowing and minimize waste of the control feed. Thereafter, subsequent to the third day after farrowing, the sows were allowed ad libitum access to the control feed until the piglets were weaned from the lactating sows. Table 3 provides a scheduling summary for the trial diets of the Control, Trial A, and Trial B.

TABLE 3

Trial Diet Schedule

| Time Period | Diet Name | Control Feed | Sorbitol (grams per day) |
|---|---|---|---|
| First 24 hours post farrowing | Control | offered 4 pounds daily | 0 |
| | Trial A | offered 4 pounds daily[a] | 26 |
| | Trial B | offered 4 pounds daily[b] | 52 |
| 24 hours to 48 hours post farrowing | Control | offered 8 pounds daily | 0 |
| | Trial A | offered 8 pounds daily[a] | 26 |
| | Trial B | offered 8 pounds daily[b] | 52 |
| 48 hours to 72 hours post farrowing | Control | offered 12 pounds daily | 0 |
| | Trial A | offered 12 pounds daily[a] | 26 |
| | Trial B | offered 12 pounds daily[b] | 52 |
| >72 hours post farrowing | Control | ad libitum | 0 |
| | Trial A | ad libitum[a] | 26 |
| | Trial B | ad libitum[b] | 52 |

[a]About two pounds of the top-dressed control feed including about 26 grams of sorbitol were provided daily in place of about two pounds of the untreated control feed.
[b]About two pounds of the top-dressed control feed including about 52 grams of sorbitol were provided daily in place of about two pounds of the untreated control feed.

The trial of this example began at farrowing when the lactating sows were fed in accordance with the schedule of Table 3. However, as noted above, the piglets were not removed from their birth sow until about forty-eight hours of birth to allow each piglet to receive colostrum from its birth sow. Thereafter, about forty-eight hours after birth (on day two after farrowing), the litters were equalized between the different sows, and the number of live nursing piglets per litter was counted and recorded.

The number of live piglets per litter was also counted and recorded fourteen days after farrowing and again at weaning. The average numbers of live piglets in the Control, Trial A, and Trial B were calculated by separately adding together the number of piglets per litter in the Control, in Trial A, and in Trial B and thereafter dividing that number of total piglets per trial (Control, Trial A, or Trial B) by the number of nursing sows in that particular trial (Control, Trial A, or Trial B). The average number of piglets per litter for each trial (Control, Trial A, or Trial B) was calculated two days after farrowing, fourteen days after farrowing, and again at weaning. The average numbers of piglets per litter at these measurement times are listed in Table 4 below for the Control, Trial A, and Trial B.

Litter mortality rates for the Control, Trial A, Trial B were separately calculated by comparing the number of piglets alive on day two post-farrowing with the number of piglets alive at day fourteen post-farrowing, with the results shown in Table 4 below as a percentage mortality during the period spanning from day two post-farrowing to day fourteen post-farrowing. Litter mortality rates for the Control, Trial A, Trial B were also separately calculated by comparing the number of piglets alive on day fourteen post-farrowing with the number of piglets alive on the day of weaning, with the results shown in Table 4 below as a percentage mortality during the period spanning from day fourteen post-farrowing to the weaning day. Finally, litter mortality rates for the Control, Trial A, Trial B were again separately calculated by comparing the number of piglets alive on day two post-farrowing with the number of piglets alive on the day of weaning, with the results shown in Table 4 below as a percentage mortality during the period spanning from day two post-farrowing to the day of weaning.

Additionally, the collective body weights of the piglets assigned to each lactating sow of the three different trials were measured and recorded on day two post-farrowing (about forty-eight hours after farrowing), on day fourteen post-farrowing (fourteen days after farrowing), and on the day the piglets were weaned. The mean body weight values for each individual piglet of the three different trials were derived for each piglet individually from the weight data recorded for each piglet litter by dividing the collective litter weight determined for a particular litter by the total number of piglets then-present in the litter to attain the mean individual piglet weights on day two post-farrowing (about forty-eight hours after farrowing), on day fourteen post-farrowing (fourteen days after farrowing), and on the day the piglets were weaned.

The data of Table 4 illustrates the effects of the sugar alcohol feedings of Trial A and Trial B, versus the absence of sugar alcohol feedings in the Control, on litter performance (piglet mortality, litter live weight, and mean individual piglet weight) for each of the three different trials (Control, Trial A, and Trial B).

TABLE 4

Litter Performance (Parity ≥ 1)

| Parameter | Trial Name | | | Coefficient of Variation | P-Value |
| | Control | Trial A | Trial B | | |
|---|---|---|---|---|---|
| Number of Sows | 20 | 21 | 21 | | |
| Mean Parity | 2.40 | 2.90 | 2.75 | 56.9 | 0.55 |
| Length of Lactation (Days) | 21.21 | 20.71 | 21.41 | 10.38 | 0.57 |

TABLE 4-continued

Litter Performance (Parity ≥ 1)

| Parameter | | Trial Name | | | Coefficient of | P-Value |
|---|---|---|---|---|---|---|
| | | Control | Trial A | Trial B | Variation | |
| Litter Performance: Number of Nursing Piglets | Day 2 | 10.65 | 10.57 | 10.50 | 7.52 | 0.83 |
| | Day 14 | 9.70 | 10.14 | 10.0 | 11.22 | 0.43 |
| | At Weaning | 9.51 | 9.95 | 10.03 | 11.44 | 0.2 |
| Litter Performance: Percentage Piglet Mortality[x] | Day 1 to Day 14 | 8.86[d] | 3.99[e] | 4.61[e] | 135 | 0.10 |
| | Day 14 to weaning | 2.09[d] | 1.74[d] | 0.00[e] | 260 | 0.09 |
| | Day 1 to Weaning | 10.75[b] | 5.69[c] | 4.60[c] | 119.2 | 0.04 |
| Litter Performance: Total Live Weight of Litter (pounds) | Day 2 | 40.80 | 43.29 | 41.17 | 21.05 | 0.62 |
| | Day 14 | 96.99 | 107.85 | 104.39 | 19.69 | 0.22 |
| | At Weaning | 137.59[d] | 147.53[de] | 154.81[e] | 17.18 | 0.09 |
| Litter Performance: Mean Weight of Individual Piglets (pounds) | Day 2 | 3.83 | 4.11 | 3.90 | 19.1 | 0.48 |
| | Day 14 | 10.03 | 10.59 | 10.39 | 15.2 | 0.53 |
| | At Weaning | 14.53 | 14.80 | 15.55 | 13.75 | 0.26 |

[b,c]Numbers within the same row with different single letter superscripts differ at a probabilily value of P < 0.05.
[d,e]Numbers within the same row with different single letter superscripts differ at a probability value of P < 0.10.
[x]Based on number of piglets present at start of measurement period The litter performance data of Table 4 demonstrates the sugar alcohol, specifically sorbitol, dosages included in Trial A and Trial B caused the health of the piglets of the Trial A litters and the Trial B litters to be improved, relative to the health of the piglets of the Control litters. One illustration of the improved health is the observation that the Trial A piglet litters and the Trial B piglet litters each exhibited lower mortality rates than the Control piglet litters, as measured over the entire pre-weaning period (measured from day one post-farrowing to weaning) and as measured over portions of the pre-weaning period (such as (1) when measured from day one post-farrowing to day fourteen post-farrowing and (2) when measured from day fourteen post-farrowing to weaning).

Another illustration of the improved health is the observation that the Trial A piglet litters and the Trial B piglet litters each exhibited increased total litter live weights as compared to the Control piglet litters, as measured over the entire pre-weaning period (measured from day one post-farrowing to weaning) and as measured over portions of the pre-weaning period (such as (1) when measured from day one post-farrowing to day fourteen post-farrowing and (2) when measured from day fourteen post-farrowing to weaning). Yet another illustration of the improved health is the observation that the Trial A piglet litters and the Trial B piglet litters each exhibited increased individual piglet mean weights versus the piglets of the Control litters, as measured over the entire pre-weaning period (measured from day one post-farrowing to weaning) and as measured over portions of the pre-weaning period (such as (1) when measured from day one post-farrowing to day fourteen post-farrowing and (2) when measured from day fourteen post-farrowing to weaning).

Specific examples about lower mortality rates that demonstrate the health improvements of the Trial A piglet litters versus the Control piglet litters are also illustrative. For example, the sugar alcohol, specifically sorbitol, dosage included in Trial A of this example resulted in a piglet mortality decrease to 3.99 percent for the Trial A piglet litters from the 8.86 percent mortality rate of the Control piglet litters (P<0.10), as measured from day one post-farrowing to day fourteen post-farrowing. Thus, the sugar alcohol dosage included in Trial A of this example caused the piglet mortality percentage to drop by 4.87 percentage points for the Trial A piglet litters versus the piglet mortality percentage of the Control piglet litters (P<0.10), as measured from day one post-farrowing to day fourteen post-farrowing. Otherwise stated, the sugar alcohol dosage included in Trial A of this example caused the piglet mortality to drop 54.97 percent {((8.86−3.99)÷8.86)×100%} for the Trial A piglet litters versus the Control piglet litters (P<0.10), as measured from day one post-farrowing to day fourteen post-farrowing.

Likewise, the sugar alcohol, specifically sorbitol, dosages included in Trial A of this example resulted in a piglet mortality decrease to 5.69 percent for the Trial A piglet litters from the 10.75 percent mortality rate of the Control piglet litters (P<0.05), as measured from, day one post-farrowing to weaning. Thus, the sugar alcohol dosage included in Trial A of this example caused the piglet mortality percentage to drop by 5.06 percentage points for the Trial A piglet litters versus the piglet mortality percentage of the Control piglet litters (P<0.05), as measured from day one post-farrowing to weaning. Otherwise stated, the sugar alcohol dosage included in Trial A of this example caused the piglet mortality to drop 47.07 percent {((10.75−5.69)÷10.75)×100%} for the Trial A piglet litters versus the Control piglet litters (P<0.05), as measured from day one post-farrowing to weaning.

Specific examples about lower mortality rates that demonstrate the health improvements of the Trial B piglet litters versus the Control piglet litters are also illustrative. For example, the sugar alcohol, specifically sorbitol, dosage included in Trial B of this example resulted in a piglet mortality decrease to 4.61 percent for the Trial B piglet litters from the 8.86 percent mortality rate of the Control piglet litters (P<0.10), as measured from day one post-farrowing to day fourteen post-farrowing. Thus, the sugar alcohol dosage included in Trial B of this example caused the piglet mortality percentage to drop by 4.25 percentage points for the Trial B piglet litters versus the piglet mortality percentage of the Control piglet litters (P<0.10), as measured from day one post-farrowing to day fourteen post-farrowing. Otherwise stated, the sugar alcohol dosage included in Trial B of this example caused the piglet mortality to drop 47.97 percent {((8.86−4.61)÷8.86)×100%} for the Trial B piglet litters versus the Control piglet litters (P<0.10), as measured from day one post-farrowing to day fourteen post-farrowing.

Next, the sugar alcohol, specifically sorbitol, dosages included in Trial B of this example resulted in a piglet mortality decrease to 0.00 percent for the Trial B piglet litters from the 2.09 percent mortality rate of the Control piglet litters (P<0.10), as measured from day fourteen post-farrowing to weaning. Thus, the sugar alcohol dosage included in Trial B of this example caused the piglet mortality percentage to drop by 2.09 percentage points for the Trial B piglet litters versus the piglet mortality percentage of the Control piglet litters (P<0.10), as measured from day fourteen post-farrowing to weaning. Otherwise stated, the sugar alcohol dosage included in Trial B of this example caused the piglet mortality to drop 100 percent {((2.09−0.00)÷2.09)×100%} for the Trial B piglet litters versus the Control piglet litters (P<0.10), as measured from day fourteen post-farrowing to weaning.

Likewise, the sugar alcohol, specifically sorbitol, dosages included in Trial B of this example resulted in a piglet mortality decrease to 4.60 percent for the Trial B piglet litters from the 10.75 percent mortality rate of the Control piglet litters (P<0.05), as measured from day one post-farrowing to weaning. Thus, the sugar alcohol dosage included in Trial B of this example caused the piglet mortality percentage to drop by 6.15 percentage points for the Trial B piglet litters versus the piglet mortality percentage of the Control piglet litters (P<0.05), as measured from day one post-farrowing to weaning. Otherwise stated, the sugar alcohol dosage included in Trial B of this example caused the piglet mortality to drop 57.21 percent {((10.75−4.60)÷10.75)×100%} for the Trial B piglet litters versus the Control piglet litters (P<0.05), as measured from day one post-farrowing to weaning.

Specific examples concerning increased total litter live weights that further demonstrate the health improvements of the Trial B piglet litters versus the Control piglet litters are also illustrative. For example, the sugar alcohol, specifically sorbitol, dosage included in Trial B of this example resulted in a total litter live weight increase to 154.81 pounds for the Trial B piglet litters versus the 137.59 pound litter live weight for the Control piglet litters (P<0.10), as measured from day one post-farrowing to weaning. Thus, the sugar alcohol dosage included in Trial B of this example caused the total litter live weight to increase by 17.22 pounds for the Trial B piglet litters versus the total litter live weight of the Control piglet litters (P<0.10), as measured from day one post-farrowing to weaning. Otherwise stated, the sugar alcohol dosage included in Trial B of this example caused the total litter live weight to increase about 12.52 percent {((154.81−137.59)÷137.59)×100%} for the Trial B piglet litters versus the Control piglet litters (P<0.05), as measured from day one post-farrowing to weaning.

In another aspect of the present invention, the mean daily feed intake for the lactating sows of the Control, Trial A and Trial B was determined for various time periods during the pre-weaning period, such as (1) day one post-farrowing through day seven post-farrowing, (2) day eight post-farrowing through day fourteen post-farrowing, (3) day one post-farrowing through day fourteen post-farrowing, (4) day one post-farrowing through day eighteen post-farrowing, and (5) day one post-farrowing through the day of piglet weaning. Each sow of the Control, Trial A and Trial B nursed piglets of the assigned litter until at least day eighteen post-farrowing. These mean daily feed intake values are presented in Table 5 below and were derived from the average daily feed intake data recorded for each lactating sow. Table 5 demonstrates the impact of the sugar alcohol, specifically sorbitol, dosages employed in Trial A and in Trial B, as compared to the Control that was free of sugar alcohol, on sow feed intake during the pre-weaning period for the sows assigned to the Control, Trial A, and Trial B.

TABLE 5

Sow Performance - Feed Intake (Parity ≥ 1)

| Parameter | | Control | Trial A | Trial B | Coefficient of Variation | P-Value |
|---|---|---|---|---|---|---|
| Number of Sows | | 20 | 21 | 21 | | |
| Mean Parity | | 2.40 | 2.90 | 2.75 | 56.9 | 0.55 |
| Length of Lactation (Days) | | 21.21 | 20.71 | 21.41 | 10.38 | 0.57 |
| Sow Feed Intake (pounds) | Day 1 thru Day 7 | 9.39 | 9.77 | 8.65 | 27.0 | 0.34 |
| | Day 8 thru Day 14 | 13.84 | 13.92 | 13.11 | 24.5 | 0.68 |
| | Day 1 thru Day 14 | 11.61 | 11.84 | 10.87 | 24.4 | 0.50 |
| | Day 1 thru Day 18 | 12.28 | 12.45 | 11.68 | 22.5 | 0.60 |
| | Day 1 thru Weaning | 12.80 | 12.91 | 12.22 | 19.9 | 0.63 |

The inventors of the present invention anticipated that sows of Trial A and Trial B that were fed the sugar alcohol dosages would exhibit a significant increase in feed intake during the pre-weaning period, as compared to the sows of the Control that were not fed any sugar alcohol. Surprisingly, however, as demonstrated by the data of Table 5, the lactating sows of Trial A and Trial B that were fed the sugar alcohol dosages did not experience any significant increase in feed intake during the pre-weaning period, as compared to the lactating sows of the Control that were not fed any sugar alcohol.

Indeed, the results of Table 5 demonstrate that feed intake actually decreased by about 0.70 pounds for the Trial B sows, as compared to the Control sow feed intake, over each of the measurement periods of the pre-weaning period. Nonetheless, this decrease in feed intake for the Trial B sows did not have a negative impact upon the mortality rates of the litters of the sows in Trial B, upon the overall litter live weights of the Trial B litter, or upon the mean piglet weight of the individual piglets of the Trial B litters, as compared to the mortality rates of the litters of the sows in the Control, the overall litter live weights of the Control litters, or the mean piglet weight of the individual piglets of the Control litters. (See Table 4 above and related discussion). Similar comments apply to the sows of Trial A of this example that generally showed a slight, insignificant feed intake versus the sows of the Control. These slight variations in feed intake of the Trial A sows and the Trial B sows, versus the feed intake of the Control sows, nevertheless correspond with lower mortality rates and increased live weights for the Trial A litters and the Trial B litters, as compared to the Control litters, and suggest the sows of Trial A and Trial B that were fed sugar alcohol produced milk more efficiently than the Control sows and therefore needed fewer calories to produce beneficial amounts of milk with beneficial nutritional composition, as compared to the sows of the Control that were not fed any sugar alcohol.

lates and eliminates (accounts for) variations of initial sow backfat thicknesses. Again, Table 6 shows the impact of the sugar alcohol fed to the sows of Trial A and Trial B versus the sows of the Control that were not fed any sugar alcohol on changes in mean back fat thickness for the sows of the Control, Trial A, and Trial B during the pre-weaning period.

TABLE 6

Sow Performance - Backfat Changes (Parity ≥ 1)

| | Parameter | Control | Trial A | Trial B | Coefficient of Variation | P-Value |
|---|---|---|---|---|---|---|
| | Number of Sows | 20 | 21 | 21 | | |
| | Mean Parity | 2.40 | 2.90 | 2.75 | 56.9 | 0.55 |
| | Length of Lactation (Days) | 21.21 | 20.71 | 21.41 | 10.38 | 0.57 |
| Sow | Day One Post-farrowing$^a$ | 0.58 | 0.70 | 0.61 | | 0.02 |
| Backfat | Adj. Day One Post-farrowing$^a$ | 0.598 | 0.598 | 0.598 | | |
| (Inches) | Weaning$^b$ | 0.584 | 0.580 | 0.567 | | 0.95 |
| | Change$^b$ | −0.014 | −0.0176 | −0.031 | | 0.95 |

$^a$Post-farrowing backfat measurements taken about 12 hours after farrowing
$^b$Post farrowing backfat was used as a covariance.

In another aspect of this example, backfat thickness for the Control sows, the Trial A sows, and the Trial B sows was individually measured and recorded on day one post-farrowing (within twelve hours of farrowing), on day fourteen post-farrowing), and on the day the piglets were weaned from the various lactating sows. Backfat thicknesses were measured using a Linear Array Ultrasound unit obtained from E.I. Medical of Loveland, Colo. in accordance with the backfat measurement instructions provided with the Linear Array Ultrasound unit. Using the backfat thickness measurements for the individual Control sows, the individual Trial A sows, and the individual Trial B sows, the mean backfat thickness for the sows of the Control, for the sows of Trial A, and for the sows of Trial B were then calculated and recorded as of day one post-farrowing (within twelve hours of farrowing), on day fourteen post-farrowing), and on the day the piglets were weaned from the various lactating sows. The results of these mean backfat thickness determinations for the sows of the Control, for the sows of Trial A, and for the sows of Trial B are tabulated in Table 6.

In this example, covariance analysis was used to increase the precision of the backfat measurements. Covariance analysis entails removing, by regression analysis, certain recognized treatment effects that cannot be or have not been effectively controlled by the experimental design. For example, if weight is correlated with weight gain, a portion of the experimental error for weight gain may be the result of differences in initial weight. Because the sows assigned to any group (such as the Control, Trial A, and Trial B) will typically vary in initial weight (and thus typically will vary in initial backfat thickness), this variation in initial backfat thickness was taken into account to help improve the accuracy of the results for changes in backfat thickness. To make each group (such as the Control, Trial A, and Trial B) of sows more comparable, backfat measurements were adjusted, via regression analysis, to more accurately estimate what the backfat measurements would have been if all the sows of the Control, Trial A, and Trial B had had the same backfat thickness at the start of the pre-weaning period of this example (i.e. on day one post-farrowing). Thus, the changes in mean backfat thickness for the sows of the Control, Trial A, and Trial B provided in Table 6 below take into account the described covariance analysis that calcu- Though not necessarily desirable, the inventors of the present invention expected the sows of Trial A and Trial B that were fed the sugar alcohol dosages would exhibit a significant decrease in backfat during the pre-weaning period, as compared to the sows of the Control that were not fed any sugar alcohol. Surprisingly, however, as demonstrated by the data of Table 6, the lactating sows of Trial A and Trial B that were fed the sugar alcohol dosages did not experience any significant backfat decrease during the pre-weaning period, as compared to the lactating sows of the Control that were not fed any sugar alcohol. Indeed, the results presented in Table 6 demonstrate the sows of Trial A and Trial B that were fed sugar alcohol lost only an insignificant amount of backfat between day one post-farrowing and weaning, as compared to the Control sows not fed any sugar alcohol. These backfat maintenance results of Table 6 further suggest the sows of Trial A and Trial B that were fed sugar alcohol produced milk more efficiently than the Control sows and therefore needed fewer calories to produce beneficial amounts of milk with beneficial nutritional composition, as compared to the sows of the Control that were not fed any sugar alcohol.

Example 2

In this example, the data from Example 1 was analyzed to remove data attributable to sows with a parity of only one. Parity refers to the number of litters a sow has previously given birth to during its life. Gilts or first-parity sows typically consume approximately fifteen to twenty percent less feed during lactation and also typically produce less milk than sows with parities greater than one. The litters of parity one sows also tend to have lower weaning weights and more health problems than the litters of sows with parities greater than one. The purpose of looking at the Example 1 data, as re-analyzed to remove the effect of parity one data, is to determine the influence of natural differences in feed intake and litter performance of parity one sows on the data presented in Example 1 above. Removing the data contributed by the seventeen parity one sows in Example 1, left the Control with fourteen sows of parity two or higher, left Trial A with sixteen sows of parity two or higher, and left Trial B with sixteen sows of parity two or higher. The remaining data contributed by the forty-five parity two or higher sows distributed between the Control, Trial A, and Trial B was analyzed and is presented as Example 2.

The data of Table 7 below illustrates the effects of the sugar alcohol feedings of Trial A and Trial B, versus the absence of sugar alcohol feedings in the Control, on litter performance (piglet mortality, litter live weight, and mean individual piglet weight) for each of the three different trials (Control, Trial A, and Trial B).

Specific examples about lower mortality rates that demonstrate the health improvements of the Trial A piglet litters versus the Control piglet litters are also illustrative. For example, the sugar alcohol, specifically sorbitol, dosage included in Trial A of this example resulted in a piglet mortality decrease to 3.52 percent for the Trial A piglet litters from the 10.73 percent mortality rate of the Control piglet litters (P<0.05), as measured from day one post-farrowing to day fourteen post-farrowing. Thus, the sugar

TABLE 7

Litter Performance (Parity ≥2)

| Parameter | | Trial Name | | | Coefficient of | P-Value |
|---|---|---|---|---|---|---|
| | | Control | Trial A | Trial B | Variation | |
| Number of Sows | | 14 | 16 | 15 | | |
| Mean Parity | | 3.02 | 3.53 | 3.48 | 37.7 | 0.49 |
| Length of Lactation (Days) | | 20.53 | 20.16 | 20.75 | 8.66 | 0.64 |
| Litter Performance: Number of Nursing Piglets | Day 2 | 10.70 | 10.51 | 10.62 | 5.86 | 0.71 |
| | Day 14 | 9.55 | 10.14 | 10.02 | 9.43 | 0.21 |
| | At Weaning | 9.34 | 10.01 | 10.02 | 10.12 | 0.12 |
| Litter Performance: Percentage Piglet Mortality$^x$ | Day 1 to Day 14 | 10.73$^b$ | 3.52$^c$ | 5.68$^c$ | 106.9 | 0.02 |
| | Day 14 to weaning | 2.33 | 1.23 | 0.00 | 285.7 | 0.17 |
| | Day 1 to Weaning | 12.77$^b$ | 4.69$^c$ | 5.71$^c$ | 103.1 | 0.01 |
| Litter Performance: Total Live Weight of Litter (pounds) | Day 2 | 42.60 | 43.37 | 44.48 | 19.56 | 0.83 |
| | Day 14 | 98.77 | 109.76 | 109.25 | 18.47 | 0.24 |
| | At Weaning | 136.59$^b$ | 150.42$^{bc}$ | 159.86$^c$ | 16.50 | 0.04 |
| Litter Performance: Mean Weight of Individual Piglets (pounds) | Day 2 | 3.97 | 4.14 | 4.18 | 18.40 | 0.74 |
| | Day 14 | 10.38 | 10.82 | 10.87 | 14.94 | 0.66 |
| | At Weaning | 14.67 | 15.02 | 16.03 | 13.73 | 0.19 |

$^{bc}$Numbers within the same row with different single letter superscripts differ at a probability value of P < 0.05.
$^x$Based on number of piglets present at start of measurement period The litter performance data of Table 7 demonstrates the sugar alcohol, specifically sorbitol, dosages included in Trial A and Trial B caused the health of the piglets of the Trial A litters and the Trial B litters to be improved, relative to the health of the piglets of the Control litters. One illustration of the improved health is the observation that the Trial A piglet litters and the Trial B piglet litters each exhibited lower mortality rates than the Control piglet litters, as measured over the entire pre-weaning period (measured from day one post-farrowing to weaning) and as measured over portions of the pre-weaning period (such as (1) when measured from day one post-farrowing to day fourteen post-farrowing and (2) when measured from day fourteen post-farrowing to weaning).

Another illustration of the improved health is the observation that the Trial A piglet litters and the Trial 13 piglet litters each exhibited increased total litter live weights as compared to the Control piglet litters, as measured over the entire pre-weaning period (measured from day one post-farrowing to weaning) and as measured over portions of the pre-weaning period (such as (1) when measured from day one post-farrowing to day fourteen post-farrowing and (2) when measured from day fourteen post-farrowing to weaning). Yet another illustration of the improved health is the observation that the Trial A piglet litters and the Trial B piglet litters each exhibited increased individual piglet mean weights versus the piglets of the Control litters, as measured over the entire pre-weaning period (measured from day one post-farrowing to weaning) and as measured over portions of the pre-weaning period (such as (1) when measured from day one post-farrowing to day fourteen post-farrowing and (2) when measured from day fourteen post-farrowing to weaning).

alcohol dosage included in Trial A of this example caused the piglet mortality percentage to drop by 7.21 percentage points for the Trial A piglet litters versus the piglet mortality percentage of the Control piglet litters (P<0.05), as measured from day one post-farrowing to day fourteen post-farrowing. Otherwise stated, the sugar alcohol dosage included in Trial A of this example caused the piglet mortality to drop 67.20 percent $\{((10.73-3.52) \div 10.73) \times 100\%\}$ for the Trial A piglet litters versus the Control piglet litters (P<0.05), as measured from day one post-farrowing to day fourteen post-farrowing.

Likewise, the sugar alcohol, specifically sorbitol, dosages included in Trial A of this example resulted in a piglet mortality decrease to 4.69 percent for the Trial A piglet litters from the 12.77 percent mortality rate of the Control piglet litters (P<0.05), as measured from day one post-farrowing to weaning. Thus, the sugar alcohol dosage included in Trial A of this example caused the piglet mortality percentage to drop by 8.08 percentage points for the Trial A piglet litters versus the piglet mortality percentage of the Control piglet litters (P<0.05), as measured from day one post-farrowing to weaning. Otherwise stated, the sugar alcohol dosage included in Trial A of this example caused the piglet mortality to drop 63.27 percent $\{((12.77-4.69) \div 12.77) \times 100\%\}$ for the Trial A piglet litters versus the Control piglet litters (P<0.05), as measured from day one post-farrowing to weaning.

Specific examples about lower mortality rates that demonstrate the health improvements of the Trial B piglet litters versus the Control piglet litters are also illustrative. For example, the sugar alcohol, specifically sorbitol, dosage included in Trial B of this example resulted in a piglet mortality decrease to 5.68 percent for the Trial B piglet litters from the 10.73 percent mortality rate of the Control piglet litters (P<0.05), as measured from day one post-farrowing to day fourteen post-farrowing. Thus, the sugar alcohol dosage included in Trial B of this example caused the piglet mortality percentage to drop by 5.05 percentage points for the Trial B piglet litters versus the piglet mortality percentage of the Control piglet litters (P<0.05), as measured from day one post-farrowing to day fourteen post-farrowing. Otherwise stated, the sugar alcohol dosage included in Trial B of this example caused the piglet mortality to drop 47.06 percent {((10.73−5.68)÷10.73)× 100%} for the Trial B piglet litters versus the Control piglet litters (P<0.05), as measured from day one post-farrowing to day fourteen post-farrowing.

Likewise, the sugar alcohol, specifically sorbitol, dosages included in Trial B of this example resulted in a piglet mortality decrease to 5.71 percent for the Trial B piglet litters from the 12.77 percent mortality rate of the Control piglet litters (P<0.05), as measured from day one post-farrowing to weaning. Thus, the sugar alcohol dosage included in Trial B of this example caused the piglet mortality percentage to drop by 7.06 percentage points for the Trial B piglet litters versus the piglet mortality percentage of the Control piglet litters (P<0.05), as measured from day one post-farrowing to weaning. Otherwise stated, the sugar alcohol dosage included in Trial B of this example caused the piglet mortality to drop 55.29 percent {((12.77−5.71)÷12.77)×100%} for the Trial B piglet litters versus the Control piglet litters (P<0.05), as measured from day one post-farrowing to weaning.

When comparing the parity ≥one data of Table 4 from Example 1 with the parity ≥two data of Table 7 from this example, one observation is that the Trial A percentage rate of litter mortality decreases, versus the Control, were noticeably larger for the parity ≥two data versus the parity ≥one data. Similar comments do not apply to the Trial B results where the percentage rate of litter mortality decreases, versus the Control, were quite similar for the parity ≥two data versus the parity ≥one data. This observation may suggest, at least for purposes of decreasing mortality in litters, the lower 26 gram per day dosage of sugar alcohol, such as sorbitol, has more beneficial impact than the higher 52 gram per day dosage of sugar alcohol, such as sorbitol.

Another observation when comparing the parity ≥one data of Table 4 from Example 1 with the parity ≥two data of Table 7 from this example is that the Trial A percentage point declines in litter mortality, versus the Control, were noticeably larger for the parity ≥two data versus the parity ≥one data. Similar comments also apply to the Trial B results, though the percentage point declines of litter mortality, versus the Control, were less dramatic for the Trial B results than for the Trial A results when comparing the parity ≥two data versus the parity ≥one data. This observation supports the prior suggestion, at least for purposes of decreasing mortality in litters, that the lower 26 gram per day dosage of sugar alcohol, such as sorbitol, has more beneficial impact than the higher 52 gram per day dosage of sugar alcohol, such as sorbitol.

An additional observation when comparing the parity ≥one data of Table 4 from Example 1 with the parity ≥two data of Table 7 from this example is that the Trial A litter mortality rate decreases to a smaller ending percentage for the parity ≥two data versus the parity ≥one data. Similar comments do not apply to the Trial B results, since the Trial B litter mortality rate, while still decreasing versus the litter mortality rate of the Control, actually decreases to a larger ending percentage for the parity ≥two data versus the parity ≥one data. This observation further supports the prior suggestion, at least for purposes of decreasing mortality in litters, that the lower 26 gram per day dosage of sugar alcohol, such as sorbitol, has more beneficial impact than the higher 52 gram per day dosage of sugar alcohol, such as sorbitol.

Specific examples about increased total litter live weights that further demonstrate the health improvements of the Trial B piglet litters versus the Control piglet litters are also illustrative. For example, the sugar alcohol, specifically sorbitol, dosage included in Trial B of this example resulted in a total litter live weight increase to 159.86 pounds for the Trial B piglet litters from the 136.59 pounds for the Control piglet litters (P<0.05), as measured from day one post-farrowing to weaning. Thus, the sugar alcohol dosage included in Trial B of this example caused the total litter live weight to increase by 23.27 pounds for the Trial B piglet litters versus the total litter live weight of the Control piglet litters (P<0.05), as measured from day one post-farrowing to weaning. Otherwise stated, the sugar alcohol dosage included in Trial B of this example caused the total litter live weight to increase about 17.04 percent {((159.86−136.59)÷136.59)×100%} for the Trial B piglet litters versus the Control piglet litters (P<0.05), as measured from day one post-farrowing to weaning.

When comparing the parity ≥one data of Table 4 from Example 1 with the parity ≥two data of Table 7 from this example, one observation is that the Trial B litter live weight gain percentage, versus the Control, were noticeably larger for the parity ≥two data versus the parity ≥one data. No meaningful comparisons are available for the Trial A parity ≥two data versus the Trial A parity ≥1one data since this data has no statistical significance relative to either the Control data or the Trial B data. Nonetheless, the available parity ≥two data versus the parity ≥one data comparison discussed above for Trial B suggests that litters of parity ≥two that are nursed from sows fed sugar alcohol, such as sorbitol, in accordance with the present invention gain weight more quickly than litters of parity ≥one that are nursed from sows fed sugar alcohol, such as sorbitol, in accordance with the present invention.

It is generally known that parity one sows typically consume less feed per day during lactation as compared to older sows. This is primarily due to the stress of farrowing a first litter. However, Table 5 shows a numeric decrease in feed intake for sows fed 52 grams of sorbitol per day. Although this decrease was not significant, concern existed over whether this decrease was related to parity one sows or common to all sows. Data from Table 5 was analyzed in the absence of feed intake data from parity one sows to form Table 8.

In another aspect of the present invention, mean daily feed intake values for the lactating sows (parity ≥two) of the Control, Trial A, and Trial B were derived from the Table 5 data of Example 1 for various time periods during the pre-weaning period, such as (1) day one post-farrowing through day seven post-farrowing, (2) day eight post-farrowing through day fourteen post-farrowing, (3) day one post-farrowing through day fourteen post-farrowing, (4) day one post-farrowing through day eighteen post-farrowing, and (5) day one post-farrowing through the day of piglet weaning and are presented in Table 8 below. The Table 8 data demonstrates the impact of the sugar alcohol, specifically sorbitol, dosages employed in Trial A and in Trial B, as compared to the Control that was free of sugar alcohol, on sow feed intake during the pre-weaning period for the sows (parity ≥two) assigned to the Control, Trial A, and Trial B.

TABLE 8

Sow Performance - Feed Intake (Parity ≥ 2)

| Parameter | | Control | Trial Name Trial A | Trial B | Coefficient of Variation | P-Value |
|---|---|---|---|---|---|---|
| | Number of Sows | 14 | 16 | 15 | | |
| | Mean Parity | 3.02 | 3.53 | 3.48 | 37.7 | 0.49 |
| | Length of Lactation (Days) | 20.53 | 20.16 | 20.75 | 8.66 | 0.64 |
| Sow | Day 1 thru Day 7 | 9.98 | 10.67 | 10.00 | 16.14 | 0.42 |
| Feed | Day 8 thru Day 14 | 14.92 | 14.87 | 14.74 | 17.27 | 0.98 |
| Intake | Day 1 thru Day 14 | 12.45 | 12.77 | 12.37 | 15.87 | 0.83 |
| (pounds) | Day 1 thru Day 18 | 13.09 | 13.31 | 13.07 | 15.18 | 0.93 |
| | Day 1 thru Weaning | 13.49 | 13.70 | 13.55 | 13.88 | 0.95 |

The inventors of the present invention, as previously discussed in Example 1, anticipated that sows of Trial A and Trial B that were fed the sugar alcohol dosages would exhibit a significant feed intake increase during the pre-weaning period, as compared to the sows of the Control that were not fed any sugar alcohol. Surprisingly, however, as demonstrated by the data of Table 8, the lactating sows of Trial A and Trial B that were fed the sugar alcohol dosages did not experience any significant increase in feed intake during the pre-weaning period, as compared to the lactating sows of the Control that were not fed any sugar alcohol. Thus, despite excluding the parity one sow data from the data of Table 8, the natural tendency of parity one sows to consume less feed as compared to parity ≥two sows did not cause any significant changes in the Table 8 results of this example versus the Table 5 results of Example 1.

Indeed, the results of Table 8 demonstrate that feed intake actually decreased by a very small amount for the Trial B sows or stayed approximately the same, as compared to the Control sow feed intake, over the different measurement periods of the pre-weaning period. Nonetheless, this decreased or similar feed intake for the Trial B sows of parity ≥two did not have a negative impact upon the mortality rates of the litters of the sows in Trial B, upon the overall litter live weights of the Trial B litters, or upon the mean piglet weight of the individual piglets of the Trial B litters, as compared to the mortality rates of the litters of the sows in the Control, the overall litter live weights of the Control litters, or the mean piglet weight of the individual piglets of the Control litters. (See Table 7 above and related discussion). Similar comments apply to the sows of Trial A of this example that generally showed a slight, insignificant feed intake versus the sows of the Control. These slight variations in feed intake of the Trial A sows and the Trial B sows, versus the feed intake of the Control sows, nevertheless correspond with lower mortality rates and increased weights for the Trial A litters and the Trial B litters, as compared to the Control litters, and suggest the sows of Trial A and Trial B that were fed sugar alcohol produced milk more efficiently than the Control sows and therefore needed fewer calories to produce beneficial amounts of milk with beneficial nutritional composition, as compared to the sows of the Control that were not fed any sugar alcohol.

In another aspect of this example, the backfat thickness data of Table 6 in Example 1 for the Control sows, the Trial A sows, and the Trial B sows was re-analyzed to removed data attributable to sows with a parity of one. The results of these mean backfat thickness determinations for the sows (parity ≥two) of the Control, for the sows of Trial A, and for the sows of Trial B sows are tabulated in Table 9 below.

In this data of Table 9, covariance analysis was again employed, as described with respect to the data of Table 6 in Example 1, to increase the precision of the backfat measurements. Thus, the changes in mean backfat thickness for the sows (parity ≥two) of the Control, Trial A, and Trial B provided in Table 9 below take into account the described covariance analysis that calculates and eliminates (accounts for) variations of initial sow backfat thicknesses that are attributable to differences in initial sow weights. Again, the data of Table 9 show the impact of the sugar alcohol fed to the sows (parity ≥two) of Trial A and Trial B versus the sows (parity ≥two) of the Control that were not fed any sugar alcohol on changes in mean backfat thickness for the sows of the Control, Trial A, and Trial B during the pre-weaning period.

TABLE 9

Sow Performance - Backfat Changes (Parity ≥ 2)

| | Parameter | Control | Trial Name Trial A | Trial B | Coefficient of Variation | P-Value |
|---|---|---|---|---|---|---|
| | Number of Sows | 14 | 16 | 15 | | |
| | Mean Parity | 3.02 | 3.53 | 3.48 | 37.7 | 0.49 |
| | Length of Lactation (Days) | 20.53 | 20.16 | 20.75 | 8.66 | 0.64 |
| Sow | Day One Post-farrowing[a] | 0.557 | 0.685 | 0.597 | 23.5 | 0.05 |
| Backfat | Adj. day one Post- farrowing[a] | 0.616 | 0.616 | 0.616 | | |
| (Inches) | Weaning[b] | 0.598 | 0.577 | 0.593 | 18.67 | 0.87 |
| | Change[b] | −0.018 | −0.039 | −0.024 | −362 | 0.87 |

[a]Post-farrowing backfat measurements taken about 12 hours after farrowing

[b]Post farrowing backfat was used as a covariance.

Though not necessarily desirable, the inventors of the present invention expected the sows of Trial A and Trial B that were fed the sugar alcohol dosages would exhibit a significant decrease in backfat during the pre-weaning period, as compared to the sows of the Control that were not fed any sugar alcohol. Surprisingly, however, as demonstrated by the data of Table 9, the lactating sows of Trial A and Trial B that were fed the sugar alcohol dosages did not experience any significant backfat decrease during the pre-weaning period, as compared to the lactating sows of the Control that were not fed any sugar alcohol. This result from the Table 9 data for the sows (parity ≥two) does not differ in any significant way from the result of the Table 6 data for the sows (parity ≥one), so parity appears to play no significant role in the quantification of backfat changes.

Indeed, the results presented in Table 9 demonstrate the sows of Trial A and Trial B that were fed sugar alcohol lost only an insignificant amount of backfat between day one post-farrowing and weaning, as compared to the Control sows not fed any sugar alcohol. These backfat maintenance results of Table 9 further suggest the sows of Trial A and Trial B that were fed sugar alcohol produced milk more efficiently than the Control sows and therefore needed fewer calories to produce beneficial amounts of milk with beneficial nutritional composition, as compared to the sows of the Control that were not fed any sugar alcohol.

Although the present invention has been described with reference to preferred embodiments, workers skilled in the art will recognize that changes may be made in form and detail without departing from the spirit and scope of the invention.

The invention claimed is:

1. A method of feeding a lactating sow, the method comprising:
    feeding the lactating sow a sugar alcohol contained in at least one of a grain-based product or an extruded feed during a period extending at least from farrowing to weaning, the sugar alcohol constituting at least 1 wt % and up to about 10 wt % of the grain-based product or extruded feed.

2. The method of claim 1, wherein the at least one of a grain-based product or an extruded feed comprises one or more of processed grains, high protein meal or fat sources.

3. The method of claim 1, wherein the sugar alcohol comprises one or more of adonitol, allitol, altritol, arabinitol, dulcitol, erythritol, glycerol, iditol, inositol, isomalt, lactitol, maltitol, mannitol, perseitol, ribitol, rhamnitol, sorbitol, threitol or xylitol.

4. The method of claim 1, wherein the lactating sow ingests, on average, at least 25 grams of sugar alcohol per day over the period.

5. The method of claim 1, wherein the sugar alcohol comprises sorbitol.

6. A method of feeding a lactating sow, the method comprising:
    feeding the lactating sow a sugar alcohol contained in at least one of a grain-based product or an extruded feed during a period extending at least from farrowing to weaning, the sugar alcohol constituting at least 1 wt % and up to about 10 wt % of the grain-based product or extruded feed, the-sow ingesting an effective amount of the sugar alcohol during the period to cause at least one piglet from a group of piglets nursing from the lactating sow to experience improved performance, wherein the effective amount of the sugar alcohol is from at least 5 grams and up to 200 grams per day.

7. The method of claim 6, wherein the at least one of a grain-based product or an extruded feed comprises one or more of processed grains, high protein meal or fat sources.

8. The method of claim 6, wherein the sugar alcohol comprises one or more of adonitol, allitol, altritol, arabinitol, dulcitol, erythritol, glycerol, iditol, inositol, isomalt, lactitol, maltitol, mannitol, perseitol, ribitol, rhamnitol, sorbitol, threitol or xylitol.

9. The method of claim 6, wherein the effective amount of the sugar alcohol averages at least 25 grams of sugar alcohol per day over the period.

10. The method of claim 6, wherein the sugar alcohol comprises sorbitol.

11. The method of claim 6, wherein the improved performance is an increased live weight at weaning of the at least one piglet.

12. A method of feeding a lactating sow, the method comprising:
    feeding the lactating sow a sugar alcohol contained in at least one of a grain-based product or an extruded feed during a period extending at least from farrowing to weaning, the sugar alcohol constituting at least 1 wt % and up to about 10 wt % of the grain-based product or extruded feed, the lactating sow ingesting an effective amount of the sugar alcohol during the period to decrease a mortality rate of a group of piglets nursing from the lactating sow, wherein the effective amount of the sugar alcohol is from at least 5 grams and up to 200 grams per day.

13. The method of claim 12, wherein the at least one of a grain-based product or an extruded feed comprises one or more of processed grains, high protein meal or fat sources.

14. The method of claim 12, wherein the sugar alcohol comprises one or more of adonitol, allitol, altritol, arabinitol, dulcitol, erythritol, glycerol, iditol, inositol, isomalt, lactitol, maltitol, mannitol, perseitol, ribitol, rhamnitol, sorbitol, threitol or xylitol.

15. The method of claim 12, wherein the effective amount of the sugar alcohol averages at least 25 grams of sugar alcohol per day over the period.

16. The method of claim 12, wherein the sugar alcohol comprises sorbitol.

* * * * *